United States Patent
Shishehchian

(10) Patent No.: US 9,992,979 B2
(45) Date of Patent: Jun. 12, 2018

(54) MIXOTROPHIC METHOD OF AQUACULTURE

(75) Inventor: Farshad Shishehchian, Singapore (SG)

(73) Assignee: Blue Aqua International PTE LTD, Singapore (SG)

(*) Notice: Subject to any disclaimer, the term of this patent is extended or adjusted under 35 U.S.C. 154(b) by 262 days.

(21) Appl. No.: 14/408,552

(22) PCT Filed: Jun. 18, 2012

(86) PCT No.: PCT/SG2012/000216
§ 371 (c)(1),
(2), (4) Date: Dec. 16, 2014

(87) PCT Pub. No.: WO2013/191642
PCT Pub. Date: Dec. 27, 2013

(65) Prior Publication Data
US 2015/0296752 A1 Oct. 22, 2015

(51) Int. Cl.
*A01K 61/00* (2017.01)
*A01K 61/10* (2017.01)
(Continued)

(52) U.S. Cl.
CPC ............ *A01K 61/00* (2013.01); *A01K 61/10* (2017.01); *A01K 61/13* (2017.01); *A01K 61/30* (2017.01);
(Continued)

(58) Field of Classification Search
CPC .... A01K 61/00; A01K 61/002; A01K 61/005; A01K 61/02; A01K 61/50; A01K 61/51;
(Continued)

(56) References Cited

U.S. PATENT DOCUMENTS 4,137,869 A * 2/1979 Kipping ............... A01K 61/60
119/230
5,353,745 A 10/1994 Fahs, II
(Continued)

FOREIGN PATENT DOCUMENTS

| CN | 101264980 A | 9/2008 |
| CN | 101885554 A | 11/2010 |
| WO | WO 2001/050845 A1 | 7/2001 |

OTHER PUBLICATIONS

McIntosh, Robins. "Changing Paradigms in Shrimp Farming: V. Estabilishing of Heterotrophic Bacterial Communities", Feb. 2001.*
(Continued)

*Primary Examiner* — Hiwot E Tefera
(74) *Attorney, Agent, or Firm* — Knobbe Martens Olson & Bear, LLP

(57) ABSTRACT

The present invention relates to a method of aquaculture of at least one farmed organism, such as fish, shrimp or any organism suitable for farming in an aquatic environment. There is provided a method of aquaculture of at least one farmed organism, the method comprising steps: (i) providing an aquatic environment comprising at least one farmed organism, phytoplankton and bacteria; (ii) providing at least one phytoplankton nutrient and at least one bacteria nutrient during a first predetermined period, allowing phytoplankton and bacteria to grow in a first predetermined phytoplankton:bacteria ratio of more than 1; (iii) providing at least one phytoplankton nutrient and at least one bacteria nutrient during a second predetermined period, allowing phytoplankton and bacteria to grow in a second predetermined phytoplankton:bacteria ratio, wherein the second predetermined phytoplankton:bacteria ratio is lower than the first predetermined phytoplankton:bacteria ratio; and (iv) providing at least one phytoplankton nutrient and at least one bacteria nutrient during a third predetermined period, allowing phy- (Continued)

toplankton and bacteria to grow in a third predetermined phytoplankton:bacteria ratio, wherein the third predetermined phytoplankton:bacteria ratio is lower than the second predetermined phytoplankton:bacteria ratio, thereby allowing the at least one farmed organism to grow.

44 Claims, 1 Drawing Sheet

(51) Int. Cl.
| | |
|---|---|
| A01K 61/13 | (2017.01) |
| A01K 61/30 | (2017.01) |
| A01K 61/50 | (2017.01) |
| A01K 61/51 | (2017.01) |
| C12N 1/12 | (2006.01) |
| C12N 1/20 | (2006.01) |
| A23K 10/16 | (2016.01) |
| A23K 10/30 | (2016.01) |
| A23K 20/00 | (2016.01) |
| A23K 50/00 | (2016.01) |
| A23K 50/80 | (2016.01) |
| A01K 61/54 | (2017.01) |
| A01K 61/59 | (2017.01) |

(52) U.S. Cl.
CPC .............. *A01K 61/50* (2017.01); *A01K 61/51* (2017.01); *A01K 61/54* (2017.01); *A01K 61/59* (2017.01); *A23K 10/16* (2016.05); *A23K 10/30* (2016.05); *A23K 20/00* (2016.05); *A23K 50/00* (2016.05); *A23K 50/80* (2016.05); *C12N 1/12* (2013.01); *C12N 1/20* (2013.01)

(58) Field of Classification Search
CPC ........ A01K 61/30; A01K 61/13; A01K 61/54; A01K 61/59; A23K 10/16; A23K 10/20; A23K 10/30; A23K 50/80; A23K 20/00; A23K 50/00; C12N 1/12; C12N 1/20
USPC ....... 119/200, 204, 207, 215, 230, 234, 242, 119/174; 47/59 R, 60, 62 N, 62 R, 1.4, 47/47, 58.1 R, 58.1 SE
See application file for complete search history.

(56) References Cited

U.S. PATENT DOCUMENTS

| | | | | |
|---|---|---|---|---|
| 5,732,653 | A * | 3/1998 | Yamine | A01K 61/59 119/204 |
| 5,801,050 | A * | 9/1998 | Uchida | C12P 1/04 435/252.1 |
| 6,327,996 | B1 * | 12/2001 | Pruder | A01K 61/59 119/207 |
| 7,467,601 | B2 * | 12/2008 | Brauman | A01K 61/00 119/224 |
| 7,482,151 | B2 * | 1/2009 | Hovanec | C07K 14/195 119/245 |
| 2003/0131800 | A1 * | 7/2003 | Yoshimura | A01K 61/00 119/200 |
| 2005/0079596 | A1 * | 4/2005 | Hovanec | C12R 1/01 435/252.3 |
| 2007/0151522 | A1 | 7/2007 | Brauman | |
| 2010/0226876 | A1 * | 9/2010 | Gregg | A61K 35/74 424/84 |
| 2012/0003705 | A1 * | 1/2012 | Jin | B01D 53/62 435/136 |
| 2012/0285392 | A1 * | 11/2012 | Morgenthaler | A01K 61/80 119/230 |

OTHER PUBLICATIONS

Hargreaves, J.A. "Photosynthetic suspended-growth systems in aquaculture" Aquacultural Engineering (2006), vol. 34, pp. 344-363.
Verschuere, L. et al. "Probiotic Bacteria as Biological Control Agents in Aquaculture" Microbiology and Molecular Biology Reviews (2000) vol. 64 (4), pp. 655-671.
Bratvold, D. et al. "Simple electrometric methods for estimating microbial activity in aquaculture ponds" Aquaculture Engineering (1998), vol. 19, pp. 29-39.
International Search Report for International Application No. PCT/SG2012/000216 dated Aug. 17, 2012.
"The Basics of Chlorophyll Measurement," Tech Note, available at http://www.ysi.com/media/pdfs/T606-The-Basics-of-Cholorophyll-Measurement.pdf, as accessed Mar. 10, 2015.
"Lab 6: Phytoplankton and Bacteria Standing Stocks," bacteria counting protocol, available at http://jochemnet.de/fiu/lab6.pdf, as accessed Mar. 10, 2015.
Diercks, et al., "Detection of Pytoplankton with Nucleic Acid Sensors," available at http://www.springerlink.com/content/v5443m2823833888/, *Algal Toxins: Nauter, Occurrence, Effect and Detection*, Springer Science + Business Media B.V. 2008.
Water Quality Products from YSI online catalog, available at http://www.ysi.com/products.php, as accessed Mar. 10, 2015.
Aquaculture Equipment Ltd, page from website, available at http://www.aquacultureequipment.co.uk, as accessed Mar. 10, 2015.
Products—Main categories of the Campbell Scientific product line web page, available at http://www.campbellsci.com.au/products, last accessed Mar. 10, 2015.
Secchi Disk Demonstration, 3:11 in length, available at http://web.archive.org/web/20150317174948/https://www.youtube.com/watch?v=yGJ5uV4jAPo, as accessed Mar. 17, 2015.

* cited by examiner

MIXOTROPHIC METHOD OF AQUACULTURE

FIELD OF THE INVENTION

The present invention relates to a method of aquaculture of at least one farmed organism, such as fish, shrimp or any organism suitable for farming in an aquatic environment.

BACKGROUND OF THE INVENTION

Aquaculture is the farming of organisms in an aquatic environment. Until the 1970s, aquaculture was not a significant contributor to the global market for seafood. However, in the last 40 years global aquaculture has expanded from an estimated 3.5 million tonnes in 1970 to about 66.7 million tonnes in 2006. Further, government restrictions to preserve populations of certain native species have increased the demand for seafood produced in controlled artificial environments such as in aquaculture ponds. The production of catfish in catfish farms is one example of the growing, large-scale aquaculture industry. Other species produced by the aquaculture industry include crayfish, oysters, shrimp, Tilapia and Striped Bass.

According to the Food and Agriculture Organization of the United Nations (FAO) Fisheries and Aquaculture Department, it is estimated that by 2012 more than 50 percent of global food fish consumption will originate from aquaculture. With aquaculture now making up a significant portion of total seafood supply, the increased production from aquaculture has also led to significant environmental impact and competition for diminishing natural resources from other sectors such as agriculture. In particular, pond production continues to dominate aquaculture production and is especially vulnerable to water scarcity. Aquaculturists have thus been under pressure to intensify production and grow more seafood with less water and land.

As aquaculture production intensified over time, providing enough oxygen in the pond environment also became a major challenge. If not enough oxygen is supplied, anaerobic conditions may appear and toxic gas production (hydrogen sulfide, ammonia) increase, affecting shrimp health and, thus, leading to disease outbreak. In the early days pond production was limited to the biomass that could be sustained with only natural weather-driven re-aeration. Over the years, first emergency aeration, then routine nightly aeration and finally 24-hour aeration was added, which is now standard practice in the industry.

However, 24-hour aeration is expensive especially in areas with limited access to electricity and/or fuel. As a general comparison, in important shrimp farming countries such as Thailand, India or Ecuador, existing aquaculture methods achieve a stocking density of 200, 100 and 30 postlarvae per square meter, respectively.

Further, even if oxygen needs are met, concentrations of nitrogenous compounds from waste decomposition often reach limiting or toxic levels. The aquatic environment may also comprise other organisms apart from the farmed organisms, such as plankton, algae and bacteria. Pathogenic or undesirable organisms may affect the growth, health and quality of the farmed species. Problems such as algal "blooms and crashes" may also be experienced at high production rates, discouraging high stocking densities. For example, a rapid growth or accumulation in the populations of unwanted algal species in the aquaculture pond, in particular blue green algae, can result in a undesirable "off flavor", causing the flesh of the fish to have an unacceptable taste and odor.

According to the FAO, China, Thailand, Viet Nam, Indonesia and India dominate the global production of shrimp and prawns. Shrimp farms may be categorized as open systems and closed systems.

Open system shrimp farms are generally open to the environment, such as open-air ponds constructed near oceans to contain and grow shrimp. These open shrimp farms suffer from vagaries of predators, the weather, diseases and environmental pollution. Saltwater from the ocean must be continually circulated through the ponds and back to the ocean to maintain adequate water chemistry for the shrimp to grow. The shrimp farmers must supply daily additions of dry food pellets to the shrimp as they grow.

Closed shrimp farms are generally self-contained aquaculture systems. While closed shrimp farms have greater control over the artificial environment contained therein, they have not been entirely satisfactory because of limited production rates, water filtration and treatment problems, and manufactured feed. Although some of these shortcomings can be overcome by increased capital expenditures, such as for water treatment facilities, the increased capital, labor and energy costs may be prohibitive.

Accordingly, there still is a need in this technical field for improved aquaculture methods, in particular methods that increase the production intensity by providing increased oxygen levels and reduced levels of nitrogenous compounds in the pond environment.

The subject matter claimed herein is not limited to embodiments that solve any disadvantages or that operate only in environments such as those described above. Rather, this background is only provided to illustrate on exemplary technology area where some embodiments described herein may be practiced.

SUMMARY OF THE INVENTION

The present invention addresses some problems in the art and provides a method of aquaculture of at least one farmed organism, wherein the farmed organism is not phytoplankton or bacteria.

According to a first aspect of the present invention, there is provided a method of aquaculture of at least one farmed organism, the method comprising steps:

(i) providing an aquatic environment comprising at least one farmed organism, phytoplankton and bacteria;

(ii) providing at least one phytoplankton nutrient and at least one bacteria nutrient during a first predetermined period, allowing phytoplankton and bacteria to grow in a first predetermined phytoplankton:bacteria ratio of more than 1;

(iii) providing at least one phytoplankton nutrient and at least one bacteria nutrient during a second predetermined period, allowing phytoplankton and bacteria to grow in a second predetermined phytoplankton:bacteria ratio, wherein the second predetermined phytoplankton:bacteria ratio is lower than the first predetermined phytoplankton:bacteria ratio; and (iv) providing at least one phytoplankton nutrient and at least one bacteria nutrient during a third predetermined period, allowing phytoplankton and bacteria to grow in a third predetermined phytoplankton:bacteria ratio, wherein the third predetermined phytoplankton:bacteria ratio is lower than the second predetermined phytoplankton:bacteria ratio, thereby allowing the at least one farmed organism to grow.

In one particular aspect, the first predetermined phytoplankton:bacteria ratio is at least about 60:40; the second predetermined phytoplankton:bacteria ratio is between about 75:25 to about 25:75; and the third predetermined phytoplankton:bacteria ratio is less than about 40:60.

According to another aspect of the present invention, there is provided an aquaculture system capable of performing the method according to any aspect of the invention, the system comprising:
(A) an aquatic environment comprising at least one farmed organism, phytoplankton and bacteria, and/or means to provide such an environment;
(B) at least one phytoplankton nutrient providing means for providing at least one phytoplankton nutrient to the aquatic environment;
(C) at least one phytoplankton nutrient sensing means for sensing at least one phytoplankton nutrient concentration in the aquatic environment;
(D) at least one bacteria nutrient providing means for providing at least one bacteria nutrient to the aquatic environment;
(E) at least one bacteria adding means for adding at least one bacteria to the aquatic environment; and
(F) at least one bacteria nutrient sensing means for sensing at least one bacteria nutrient concentration in the aquatic environment.

BRIEF DESCRIPTION OF THE FIGURES

The accompanying figures, which are incorporated in and constitute a part of this specification, illustrate aspects of the invention and, together with a general description of the invention given above, and the detailed description given below, serve to explain the invention.

DETAILED DESCRIPTION OF THE INVENTION

Figure 1:
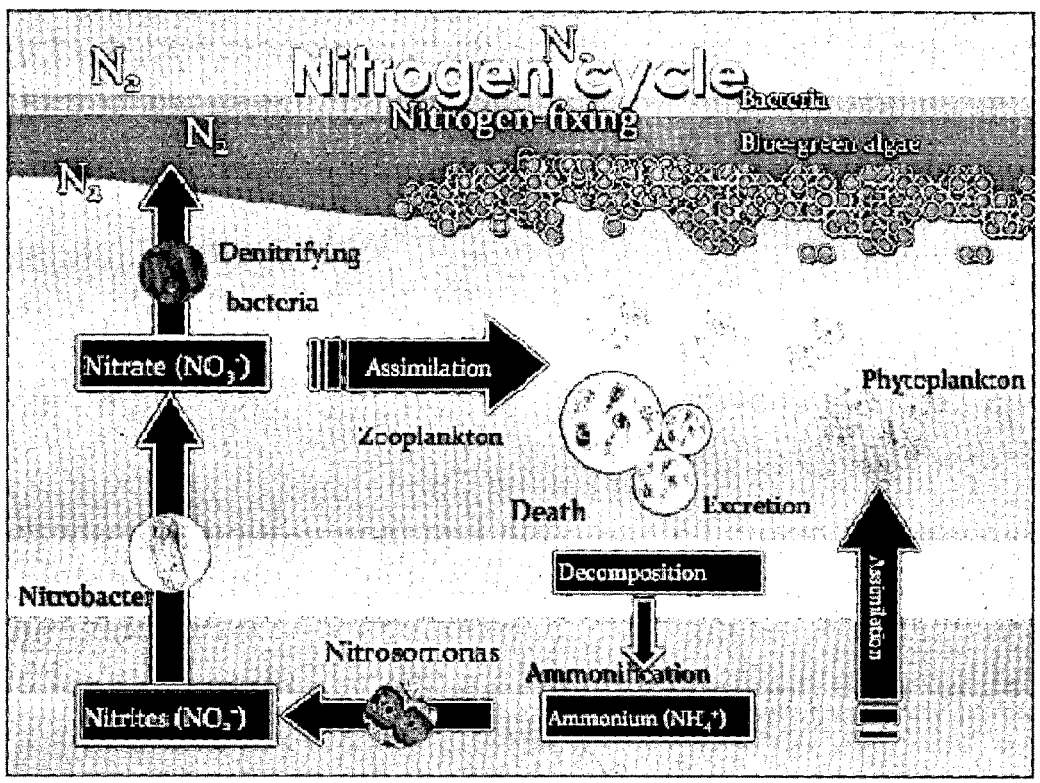
FIG. 1 is a simplified diagram illustrating the general nitrogen cycle in an aquatic environment, for example in an aquaculture pond.

It is to be understood by one of ordinary skill in the art that the present disclosure is a description of exemplary embodiments and is not intended to limit the present invention, which comprises broader aspects embodied in the exemplary constructions.

Accordingly, the present invention addresses some problems in the art and provides a method of aquaculture of at least one farmed organism.

In general, the present invention is directed to a method of aquaculture of at least one farmed organism. For the purposes of this specification, a farmed organism is any commercially grown or cultivated species produced by means of aquaculture such as any animal or plant produced by means of aquaculture such as fish, crustacean, mollusc, seaweed and/or invertebrate. Exemplary types of Fish include Tilapias, Catfishes, Milkfishes, Groupers, Barramundi, Carps, Snakeheads, Catlas, Sturgeons, Eels, Mullets, Rohus, Seabasses, Seabreams, Rabbit fishes. Exemplary Crustaceans include Shrimps, Prawns, Crabs, Lobsters, Crayfishes. Exemplary Molluscs include Oysters, Clams, Mussels, Scallops, Carpet shells, Abalones. Exemplary invertebrates may include Sea cucumbers, Sea urchins.

For the purposes of this specification, a farmed organism may also be referred to as a primary organism or a primary farmed organism. There may be one or more farmed organisms in a given aquatic environment.

In particular, the system of the present invention is particularly well suited for raising fish and/or shrimp. Thus, much of the remaining description may be directed to embodiments wherein the farmed organism is fish and/or shrimp. It should be understood, however, that the system is also well suited for raising other aquatic farmed organisms.

According to a first aspect of the present invention, there is provided a method of aquaculture of at least one farmed organism, the method comprising steps:
  (i) providing an aquatic environment comprising at least one farmed organism, phytoplankton and bacteria;
  (ii) providing at least one phytoplankton nutrient and at least one bacteria nutrient during a first predetermined period, allowing phytoplankton and bacteria to grow in a first predetermined phytoplankton:bacteria ratio of more than 1;
  (iii) providing at least one phytoplankton nutrient and at least one bacteria nutrient during a second predetermined period, allowing phytoplankton and bacteria to grow in a second predetermined phytoplankton:bacteria ratio, wherein the second predetermined phytoplankton:bacteria ratio is lower than the first predetermined phytoplankton:bacteria ratio; and
  (iv) providing at least one phytoplankton nutrient and at least one bacteria nutrient during a third predetermined period, allowing phytoplankton and bacteria to grow in a third predetermined phytoplankton:bacteria ratio, wherein the third predetermined phytoplankton:bacteria ratio is lower than the second predetermined phytoplankton:bacteria ratio,
  thereby allowing the at least one farmed organism to grow.

It may thus be seen that the method of the present invention may proceed via a production cycle that may comprise at least a first, a second and a third predetermined period. These three periods may be differentiated by the aquatic environment having:
  In the first period, phytoplankton in greater abundance than bacteria;
  In the second period, phytoplankton and bacteria in a ratio less than that in the first period; and
  In the third period, phytoplankton and bacteria in a ratio less than that in the second period.

In some embodiments, each of the first, second and third predetermined ratios may be more than about 1. In other embodiments, the second and/or third predetermined ratios may be less than about 1. For example, during the third period bacteria may be present and/or allowed to grow in greater abundance than plankton.

In one particular aspect, the first predetermined phytoplankton:bacteria ratio is at least about 60:40; the second predetermined phytoplankton:bacteria ratio is between about 75:25 to about 25:75; and the third predetermined phytoplankton:bacteria ratio is less than about 40:60.

For example, in some embodiments of the present invention the phytoplankton and bacteria may be allowed to grow in a phytoplankton:bacteria ratio of 90:10 during the first predetermined period. In such embodiments, the phytoplankton:bacteria ratio allowed in the second predetermined period may be between about 75:25 to about 25:75. In other embodiments, the phytoplankton:bacteria ratio allowed in the first predetermined period may be 60:40, and accordingly the phytoplankton:bacteria ratio allowed in the second predetermined period may be lower than that in the first predetermined period, i.e. between about 60:40 to about 25:75. Similarly, the phytoplankton:bacteria ratio allowed in the third predetermined period may be lower than that allowed in the second predetermined period.

In certain preferred embodiments, in the second period phytoplankton and probiotic bacteria are present and/or allowed to grow in roughly equal proportions.

The relative abundance of phytoplankton and bacteria is manipulated by regulating both inorganic matter (minerals and nutrients provided) and organic matter (mainly coming from feeding but also faeces and shrimp moulds) in the water, also including any organic carbon source added to the water.

However, the actual phytoplankton:bacteria ratio may be difficult and/or costly to determine accurately. In a laboratory phytoplankton may be counted using a microscope counting chamber, which is also able to determine what species of phytoplankton are present in the water. However, counting cell concentrations in a farm may be very time-consuming. One technique to indirectly measure phytoplankton concentration may be to measure the amount or concentration of chlorophyll in the aquatic environment by measuring its fluorescence. This may be done in the lab or using a fluorescence probe such as the aquatic probes described in http://www.ysi.com/media/pdfs/T606-The-Basics-of-Chlorophyll-Measurement.pdf which may be deployed on or in the aquatic environment. However, using such probes may be too costly, require skilled operators, and/or otherwise be impractical for many aquaculture farms. Accordingly, many aquaculture farms normally use a Secchi disk visibility reading to estimate phytoplankton populations in the water.

As elaborated on later, a Secchi disk is submerged in the water and depending on the depth (in centimeters) that it disappears, the phytoplankton concentration may be estimated. A video example is available at http://www.youtube.com/watch?v=yGJ5uV4jAPo. If Secchi disk gives a measurement of 50 cms, water has a low phytoplankton concentration, while 20-30 cms depth is a high phytoplankton concentration and nutrients should not be applied at this time, otherwise excessive phytoplankton bloom may be induced, which is harmful. Water colour is also very important, the method of the present invention induces a brownish green colour water, which may be due to the combined pigmentation effect of the groups of organisms allowed to grow.

There is also a laboratory methodology for bacterial counting which is even more time-consuming, it requires bacterial culture and special equipment. One example of a bacteria counting protocol may be found at http://www.jochemnet.de/fiu/lab6.pdf. As the skilled person may appreciate, bacteria populations are difficult to quantify, and the data obtained depends heavily on the type and number of bacteria culture media used. Further, this method may not be accurate as some bacteria may not be reliably cultivable on standard media. Some techniques may count only the populations of one or a few types of common bacteria, or types of bacteria known to be beneficial to the farmed organism (probiotic bacteria). However, bacteria culture techniques may be too time-consuming and impractical for a dynamic determination of bacteria growth and populations. There may also be more efficient high-throughput techniques such as epifluorescence flow cytometry, but again, such techniques may be too costly or require too much skill for many farms to operate cost-effectively. Instead, on most aquaculture farms, aquaculturists follow environmental observations such as foam in the water surface. For example, using the method of the present invention, white coloured foam may appear on the surface of the aquatic environment during the third predetermined period, possibly indicating that bacteria are becoming more dominant. Preferably, this occurs at the start of the third predetermined period. In some embodiments, it may be possible that the foam appears toward the end of the second predetermined period.

In some embodiments of the invention, the steps of the invention are sequential, in that the second step starts after the end of the first step, the third step after the second step, and so on. In other embodiments of the invention, the steps of the invention are not necessarily sequential, in that some steps may occur simultaneously with one or more other steps. For example, some embodiments may comprise further steps of providing and/or adding inputs such as minerals or bacteria. Such further steps may take place across at least part of one predetermined period, preferably over more than part of one predetermined period, more preferably over at least two predetermined periods, most preferably over the first, second and third predetermined periods.

In some embodiments of the present invention, the at least one phytoplankton nutrient and at least one bacteria nutrient may be provided during the first, second and third predetermined periods at respective concentrations suitable to grow phytoplankton and bacteria in the first, second and third predetermined phytoplankton:bacteria ratios. For example, they may be provided at a concentration suitable to grow phytoplankton and bacteria in a phytoplankton:bacteria ratio of:

at least about 60:40 during the first predetermined period;
between about 75:25 to about 25:75 during the second predetermined period; and
less than about 40:60 during the third predetermined period.

Different concentrations of nutrients may be needed to promote different groups of desired phytoplankton and bacteria most suitable and beneficial to the farmed organisms. To provide nutrients at a certain concentration, an aquaculture system may be used that may comprise nutrient sensing means operatively coupled to nutrient providing means, for example sensors to sense concentrations of substances in the water, that may indicate when further nutrient should be provided to the water, for example by using an automatic nutrient dispenser device.

For the purposes of the present specification, "aquatic environment" refers to water bodies that serve as habitat for interrelated and interacting communities and populations of plants and animals, further comprising any layer of organic matter and/or any cavity in fluid communication with the water phase. For example, in a typical earthen aquaculture pond the aquatic environment comprises both the water phase and the soil phase lining the bottom and sides of the pond.

"Pond" refers to an aquatic environment where farmed species are held or cultured. In conventional fish farming, the pond is the place where juvenile fish are raised to market size. A typical pond is earthen-bottomed but other materials may also be used to form the pond, for example ponds which are concrete- or plastic-bottomed are also understood to be suitable aquatic environments for the purposes of the present invention.

Aquatic environments typically also comprise organisms such as phytoplankton and bacteria. When used for aquaculture, at least one farmed organism is introduced into the aquatic environment, in a process known as "stocking".

Phytoplankton are minute plants suspended in water with little or no capability of controlling their position in the water mass; they may comprise microalgae and may serve as food for the at least one farmed organism. "Bacteria" may comprise any form of bacteria including bacterial spores and bacterial seed. Bacteria may be present in aquatic environments used for aquaculture and may further be present in or grow to colonize plants and animals in the aquatic environment. For example, some bacteria may be present in the intestinal systems of the at least one farmed organism, or grow to be present therein. Some phytoplankton or bacteria may grow to a level where they are undesirable or harmful to the health of the farmed organisms, for example by releasing certain harmful substances into the aquatic environment. However, the growth of other phytoplankton and bacteria may be beneficial to the health of the farmed organisms.

For the purposes of the present specification, "period" refers to a period of time.

"Nutrient" refers to substances that are beneficial to the growth of an organism. For example, "phytoplankton nutrient" refers to substances which encourage or promote the growth of phytoplankton and "bacteria nutrient" refers to substances which encourage or promote the growth of bacteria. Optimal growth may refer to achieving a high growth rate and/or healthy growth such that the phytoplankton and/or bacteria improve the growth of the farmed organisms. For example, optimally grown phytoplankton may provide better nutrition to the farmed organisms. Different organisms require different nutrients to grow, and in particular each organism requires a different composition of nutrients to grow optimally. The composition of nutrients that promotes the optimal growth of green algae may differ from that required for optimal growth of blue-green algae. Similarly, different groups of bacteria grow best in environments of different nutrient compositions, and different farmed organisms have different nutritional needs for optimal growth.

For the purposes of the present invention, phytoplankton and bacteria are allowed to grow during different predetermined periods in certain phytoplankton:bacteria ratios. Each ratio is meant as a guide to the relative abundance of phytoplankton compared to bacteria which will provide an environment most beneficial to the growth of the farmed organisms. It should be understood that the invention is not limited to growth in the exact ratios specified, as the best phytoplankton:bacteria ratios for each predetermined period may vary depending on the farmed organism and on the types of phytoplankton and bacteria present in the aquatic environment. To grow in a certain ratio may refer to growth in terms of increase in the mass of the respective organisms or in the mass thereof. To grow in a certain ratio may also refer to growing such that the ratio of the respective organisms is achieved during the period specified. The ratios may relate to the relative abundance of phytoplankton and bacteria in terms of mass of organisms or number of organisms. For example, one ratio may be 60:40, which may mean that of the total number or mass of phytoplankton and bacteria, 60% may be due to phytoplankton and 40% may be due to bacteria. Growth in this ratio is achieved by, inter alia, controlling the composition of nutrients provided in the aquatic environment. However, the phytoplankton and bacteria may not be present at this ratio at all times during the predetermined period. The actual ratio of phytoplankton:bacteria present changes gradually over time as growth rates for each type of phytoplankton and bacterium adjust to any changes in nutrient availability and other environmental parameters, for example dissolved oxygen, temperature and intensity of sunlight. Both the growth of the organisms and the numbers in which they are present may be tedious to establish directly, thus for the purposes of this specification they may be measured indirectly, for example through water visibility readings, concentrations of their metabolites or resource consumption, for example change in dissolved oxygen, and the like.

In some embodiments of the present invention, the at least one phytoplankton nutrient may be provided during the first, second and third predetermined periods in decreasing concentrations suitable to grow phytoplankton and bacteria in the first, second and third predetermined phytoplankton:bacteria ratios. For example, phytoplankton nutrients may be provided in decreasing concentrations suitable to grow phytoplankton and bacteria in a phytoplankton:bacteria ratio of:
at least about 60:40 during the first predetermined period;
between about 75:25 to about 25:75 during the second predetermined period; and
less than about 40:60 during the third predetermined period.
The concentration of the phytoplankton nutrients may be gradually decreased over the first, second and third predetermined periods, in any combination of a stepwise, linear, and/or exponential decrease. Further, the decrease may be dynamically moderated in response to certain measurable parameters, such as, but not limited to, dissolved oxygen, dissolved nitrogenous compounds, dissolved phosphorous-containing compounds and Secchi disk visibility. For example, if the Secchi disk visibility indicates that the phytoplankton is not growing sufficiently to achieve the desired phytoplankton:bacteria ratio, more phytoplankton nutrients may be provided, raising the phytoplankton nutrient concentration and promoting the growth of phytoplankton such that phytoplankton and bacteria are allowed to grow in the desired ratio. Further, the decrease may be moderated in response to certain easily observable but less easily measurable indicators such as the colour of the water in the aquatic environment. Under normal conditions of growth when using the method of the present invention, the water in the aquatic environment may preferably be green, brown, light brown, or brownish green in colour. Preferably, the water is brownish green in colour. However, in some instances green coloured water or other colours of water may indicate an algal bloom of harmful phytoplankton such as blue-green algae, and the decrease in concentration of phytoplankton nutrient may be moderated to mitigate this. If desired, it may also be possible in some embodiments to use at least one bacteria sensing means such as an apparatus capable of counting and identifying the various types of bacteria. Such an apparatus may for example comprise a genetic analysis device such as the one envisioned in http://www.springerlink.com/content/v5443m2823833888/. However, in most cases the use of such devices may not presently be possible on a wide scale due to cost reasons:

In some embodiments of the present invention, the at least one bacteria nutrient may be provided during the first, second and third predetermined periods in increasing concentrations suitable to grow phytoplankton and bacteria in the first, second and third predetermined phytoplankton:bacteria ratios. For example, the bacteria nutrients may be provided in increasing concentrations suitable to grow phytoplankton and bacteria in a phytoplankton:bacteria ratio of:
at least about 60:40 during the first predetermined period;
between about 75:25 to about 25:75 during the second predetermined period; and
less than about 40:60 during the third predetermined period.
The concentration of the bacteria nutrients may be gradually increased over the first, second and third predetermined periods, in any combination of a stepwise, linear, and/or exponential increase. The increase may also be dynamically moderated in response to certain measurable parameters, such as, but not limited to, dissolved oxygen, dissolved nitrogenous compounds and dissolved organic carbon. Further, the increase may be moderated in response to certain easily observable but less easily measurable indicators such as the colour and appearance of foam on the surface of the aquatic environment. Under normal conditions of growth when using the method of the present invention, foam may appear during the third predetermined period, which may indicate that bacteria populations are becoming predominant in the aquatic environment. Preferably, the foam may be white in colour. Accordingly, to give an example, if the expected occurrence of foam does not develop in the third predetermined period, this may indicate that bacteria are not growing fast enough to become dominant and so an aquaculturist may decide to provide more bacteria nutrients, raising the bacteria nutrient concentration and promoting the growth of bacteria such that phytoplankton and bacteria are allowed to grow in the desired ratio.

In some embodiments of the present invention, the method may further comprise adding bacteria to the aquatic environment, wherein the added bacteria is capable of maintaining the concentration of ammonia and/or nitrites and/or nitrates in the aquatic environment at a level that is not toxic to the at least one farmed organism and/or wherein the bacteria is not toxic or pathogenic to the at least one farmed organism. The bacteria may be added during the first, second and third predetermined periods in increasing concentrations suitable to allow phytoplankton and bacteria to grow in the first, second and third predetermined phytoplankton:bacteria ratios. For example, the bacteria may be added in increasing concentrations suitable to allow phytoplankton and bacteria to grow in a phytoplankton:bacteria ratio of:

at least about 60:40 during the first predetermined period; between about 75:25 to about 25:75 during the second predetermined period; and
less than about 40:60 during the third predetermined period. As with embodiments wherein the concentration of bacteria nutrient is gradually increased, the increase in added bacteria may also be dynamically moderated in response to certain measurable parameters, and/or certain easily observable but less easily measurable indicators such as the colour and appearance of foam on the surface of the aquatic environment.

The invention manages pond soil and sediment, and improves water and effluent quality, minimizing environmental impact. Survival rate of the farmed organism is improved and risk of failure due to disease or low production is minimized, and less chemical compounds are required. These benefits come in part due to the beneficial bacteria that reduce build up of decomposing organic matter, thus avoiding excessive increase in biological oxygen demand (BOD), while simultaneously out competing and suppressing growth in populations of toxic and/or harmful bacteria.

Accordingly, it may be understood by a skilled aquaculturist that a gradually decreasing concentration of phytoplankton nutrients are provided to have more phytoplankton during the first predetermined period and gradually decrease its concentration in the second and third predetermined periods. A gradually increasing concentration of bacteria nutrients are provided and a gradually increasing amount of bacteria are added to increase their population gradually over the first, second and third predetermined periods. Thus, over this time there is a shift from phytoplankton to bacterial predominance.

The desired phytoplankton:bacteria ratios for each predetermined period may vary depending on the farmed organism and on the types of phytoplankton and bacteria present in the aquatic environment. In some embodiments of the present invention, phytoplankton and bacteria may be allowed to grow in a first predetermined phytoplankton:bacteria ratio of at least about 65:35 during the first predetermined period. In particular embodiments, this ratio may be at least about 70:30, preferably at least about 75:25, more preferably at least about 80:20. In yet more preferred embodiments, this ratio may be at least about 85:15, more preferably 90:10. In some particular embodiments, this ratio may be about 95:5.

In some embodiments of the present invention, phytoplankton and bacteria may be allowed to grow in a second predetermined phytoplankton:bacteria ratio of between about 70:30 to about 30:70 during the second predetermined period. More preferably, this ratio may be between about 65:35 to about 35:65, yet more preferably about 60:40 to about 40:60. In particular preferred embodiments, the ratio may be between about 55:45 to about 45:55. In some particular preferred embodiments, the phytoplankton and bacteria may be equally dominant, i.e. this ratio may be about 50:50.

In some embodiments of the present invention, the third predetermined ratio may be lower than the second predetermined ratio, which may be lower than the first predetermined ratio, which may be more than 1. For example, the first, second and third predetermined ratios may be 90:10, 75:25 and 50:50, respectively. In another example, the first, second and third predetermined ratios may be 75:25, 50:50 and 25:75 respectively.

Methods of aquaculture known in the art control basically phytoplankton growth, even if there is probiotic application, farmers do not follow any protocol to maintain bacteria populations. Only phytoplankton is promoted to grow in the traditional shrimp farming technique.

Aquaculture methods known in the art also maintain phytoplankton growth at levels resulting in Secchi Disk readings from 30-35 cm. This may be as more phytoplankton is perceived to represent more abundant food for the farmed organisms, and thus seen to be beneficial. However, the inventors have found that this may lead to problems which may be due to increased biological oxygen demand from decomposition of dead plankton and hypoxic conditions for the farmed organism.

Often phytoplankton excessively blooms leading to phytoplankton crash and anaerobic conditions afterwards. There is a high oxygen demand from bacteria when phytoplankton crashes, because they decompose dead phytoplankton. If not enough oxygen is supplied, anaerobic conditions may appear and toxic gas production (hydrogen sulfide, ammonia) increase, affecting shrimp health and, thus, leading to disease outbreak.

Instead, the inventors have found surprisingly that having less phytoplankton and reducing the phytoplankton populations in relation to bacteria populations may be beneficial for the farmed organisms. Accordingly, in some embodiments of the present invention, phytoplankton may be allowed to grow such that the aquatic environment has a Secchi disk visibility of between about 60 cm to about 30 cm during the first predetermined period;

the aquatic environment has a Secchi disk visibility of between about 40 cm to about 20 cm during the second predetermined period; and the aquatic environment has a Secchi disk visibility of between about 70 cm to about 60 cm during the third predetermined period.

Secchi Disk Visibility: The Secchi disk visibility test is a commonly used measurement of water quality and plankton abundance in pond aquaculture. A standard Secchi disk is a 20-cm-diameter disk with alternate black and white quadrants. It is attached to a calibrated line and fitted with a weight so it will sink rapidly. At the point that the Secchi disk disappears from sight, the length of the line from the water surface to the top of the Secchi disk is measured. This is the Secchi Disk visibility. Secchi disk visibility usually is reported in centimeters, and may vary widely from a few centimeters to several meters. Generally, there is enough light for plant growth down to about twice the Secchi disk visibility. Thus, twice the Secchi disk visibility is a rough estimate of the depth of the photic zone in lakes, ponds, and other water bodies.

Secchi disk visibility is correlated strongly with water turbidity and may be affected by suspended particles of soil sediment. In this regard, the skilled person may have to take into account a background Secchi disk visibility in assessing water turbidity due to plankton abundance. The test is commonly used in aquaculture to evaluate plankton abundance and as an indicator of the need for fertilizer application in fish or shrimp culture to encourage plankton growth. Changes in Secchi disk visibility over time are also important to indicate changes in abundance of plankton.

The passage of light through a column of water is described by the equation:

$$\text{Light at depth } z = \text{Incident light} \times e^{-kz}$$

Where e=base of the natural logarithm (2.303),
k=the extinction coefficient, and z=depth in meters.

It has been shown that the extinction coefficient is related closely to Secchi disk visibility in meters: k=1.7/Secchi disk visibility in meters.

Because Secchi disk visibility is used to compare clarity among water bodies, a standard procedure must be followed in its measurement or serious errors in interpretation may occur. Guidelines for proper Secchi disk visibility measurement include, for example:

The disk should be slowly lowered until it just disappears from view a first measurement made. It should then be raised until it just reappears. The average of the two measurements should be used as the Secchi disk visibility.

The measurement should be made on clear or partly cloudy days when the sun is not obscured by clouds and the reading should be taken with the sun behind the observer.

The observer's face should be within 25-50 cm above the water surface while making the reading and the observer should not wear sunglasses while making the measurement.

In some embodiments of the present invention, the method may further comprise the step of providing at least one additional feed for the at least one farmed organism to grow, the additional feed being provided in a ratio of 1:A:B in the first, second and third predetermined periods respectively, wherein A is between about 3 to about 15 and/or B is between about 10 to about 30. In particular embodiments, A may be between about 5 to about 10 and/or B may be between about 15 to about 20. The skilled aquaculturist would understand that the ratios of additional feed being provided may refer to a cumulative amount or a dosage rate, and that both the cumulative amount and dosage rate of the additional feed depend on the species of farmed organism and the stocking density. For example, in shrimp farming at a stocking density of at least about 200 postlarvae per square meter of pond size, the at least one additional feed may be provided at a daily rate of between about 5 kg to about 15 kg during the first predetermined period, at a daily rate of between about 15 kg to about 75 kg during the second predetermined period, and between about 50 kg to about 150 kg during the third predetermined period. If the first, second and third predetermined periods are of equal length, the cumulative amounts of additional feed would be in ratios similar to the ratio of the dosage rates. However, if the predetermined periods are of differing length, the cumulative amounts of additional feed may not be in the same ratio as the ratio of the dosage rates. These dosage rates and cumulative amounts should thus be adjusted according to the requirements of the particular farmed organisms.

For the purposes of this application, the term "feed" refers to any food source provided for the at least one farmed organism. For example, in addition to the phytoplankton and/or bacteria provided in the method of the present invention, at least one additional feed may be provided. This feed may be of different forms and ingredients suitable for allowing the growth of the at least one farmed organism. For example, the feed may comprise a mixture of products of vegetable or animal origin in their natural state, fresh or preserved, or products derived from the industrial processing thereof, or organic or inorganic substances, whether or not containing additives. Feed may be provided in different forms, such as compressed sinking pellet, extruded floating pellet, granular, crumble, extruded soft pellet and other forms. One example of a feed for fish is fishmeal, a protein-rich feed derived from processing whole fish (usually small pelagic fish and by catch from fishing activities) as well as residues and by-products from fish processing plants such as fish offal.

Minerals and vitamins are essential to the healthy growth of farmed organisms, phytoplankton and bacteria. Minerals may comprise elements needed in trace amounts or larger amounts for healthy growth in these organisms. For example, minerals such as zinc, calcium, iron, magnesium, manganese and so forth are involved in certain enzymes and are essential for maintenance of life in man, animals and plants. In some instances, vitamins facilitate the incorporation of the mineral into the enzyme such that enzyme activity is inhibited by a shortage in the mineral or in the vitamin. For example, zinc is involved in the synthesis of DNA by the zinc-containing enzyme DNA polymerase. The vitamin niacin facilitates incorporation of zinc into the peptide subunits of the DNA polymerase enzyme. If either niacin or zinc is deficient in the body, DNA polymerase activity of the tissues may be reduced and the result in both cases is lack of growth. In methods of aquaculture where the stocking density is high, it is therefore important to provide the required minerals and vitamins in a form that may be efficiently taken up by the organism, i.e. a bioavailable form. To provide some non-limiting examples, bioavailable forms may include forms such as a salt that is readily soluble in water, a floating pellet that the farmed organisms may ingest, a slow-release form which is able to release a constant amount of the vitamins and/or minerals into the aquatic environment for consumption and assimilation by the farmed organism, phytoplankton and/or bacteria, and the like. In addition, some minerals are able to provide a buffering effect in water to maintain the pH of the aqueous or aquatic environment within a certain range. For example, the mineral may comprise a reservoir of alkaline metal ions which are able to dissolve in a slightly acidic medium, such that when the pH of the aquatic environment decreases, more alkaline metal ions dissolve into the aquatic environment from the mineral, such that the pH is maintained within a certain range. The pH changes may be due to changes in dissolved carbon dioxide resulting from photosynthesis and respiration in the day and night, respectively. Such a buffering effect may be useful in reducing stress levels of the farmed organisms.

Accordingly, in some embodiments of the present invention the method may further comprise the step of providing at least one mineral and/or vitamin, wherein the at least one mineral and/or vitamin is in a bioavailable form suitable for allowing the at least one farmed organism, the phytoplankton and/or the bacteria to grow. The at least one mineral and/or vitamin may be provided in a gradually increasing amount suitable for allowing the at least one farmed organism, the phytoplankton and/or the bacteria to grow. The at least one mineral may be provided in an amount suitable for maintaining the pH of the aquatic environment between about 7.5 to about 8.5. The at least one mineral may be provided across at least part of one predetermined period. Preferably, the at least one mineral may be provided over at least two predetermined periods, more preferably, over the first, second and third predetermined periods.

Beneficial and non-toxic phytoplankton include some green algae and diatom species, which may be highly nutritious for the farmed organisms. Different aquatic environments may comprise different species of green algae and diatoms according to the environment. Accordingly, in some embodiments of the present invention, the phytoplankton allowed to grow may comprise at least one green algae and/or at least one diatom species.

Some species of bacteria may be probiotic with respect to the farmed organism, meaning that they confer improved health and growth on a host, which is the farmed organism. Such probiotics may be administered as a live microbial feed supplement where the farmed organism benefits by the improvement of the balance of its intestinal microbial flora, and enzymes and vitamins produced by microbial supplement. These bacteria may also colonize the environment, i.e. water and soil phases, suppressing pathogen growth in it, in addition to enhancing protection against disease. They may also play an important role in decomposing organic matter.

Accordingly, in some embodiments of the present invention, at least one of the added bacteria and/or the bacteria allowed to grow may comprise at least one species of bacteria that is probiotic with respect to the at least one farmed organism.

Aquaculture production modifies water biochemistry, increasing organic matter and nitrogenous compounds in the aquatic environment:

Feeding increases organic matter and nitrogen concentration.

Shrimps produce organic matter (faeces, uneaten feed, moulting shell), ammonia and urea, excreted by gills and faeces, respectively.

There is an increase in natural food, phytoplankton and zooplankton, which serves as additional source of food for shrimp but also contributes to organic matter of the pond.

As decomposition of the organic matter in the pond requires oxygen and releases nitrogenous compounds, oxygen demand and the concentration of nitrogenous compounds both increase in relation to the stocking intensity.

Microorganisms such as bacteria and phytoplankton influence nutrient cycles in the water and soil interphase, and indirectly, water quality parameters and its stability, important for aquaculture production. Sulphur, silicon, phosphorus and nitrogen biochemical cycles in the pond, are strongly unbalanced when aquaculture farms operate, i.e. inputs of feeding, shrimp metabolism, etc.

Of these, the nitrogen cycle is determinant. The nitrogen cycle is very important because many organisms are involved in it and aquaculture activity strongly modifies it. Too high a level of nitrogenous compounds in the pond environment can be toxic to the farmed organism, e.g. shrimp.

The nitrogen cycle is influenced by biochemical activities of phytoplankton, bacteria and the farmed organism. These up- and down-regulate nitrogen compounds concentration in the water by their biological activity as can be seen in FIG. 1:

Ammonification is the conversion of organic matter (uneaten feed, faeces, dead phytoplankton, moults) into ammonia (NH4) and it is carried out by heterotrophic bacteria under aerobic and anaerobic conditions. Heterotrophic bacteria (later called probiotics) decompose organic matter into ammonia, decreasing biological oxygen demand, and thus preventing anaerobic conditions that will induce hydrogen sulfide (H2S) production by a different type of bacteria.

Nitrification is the conversion of ammonia into nitrite (NO2) and then into nitrates (NO3) by nitrifying bacteria, *Nitrosomonas* and *Nitrobacter* species, respectively under aerobic conditions. Ammonia and nitrites are toxic at certain levels.

Assimilation of ammonia and nitrates by the phytoplankton reduces toxicity of nitrogenous compounds. Phytoplankton photosynthetic activity reduces CO2 concentration in the water at daytime increasing pH, whilst at nightime respiration produces the opposite effect. Maintaining a proper bloom (abundance and species) of phytoplankton balances pond water pH and temperature.

Denitrification is the conversion of nitrates to atmospheric nitrogen (N2) by denitrifying bacteria.

Atmospheric nitrogen is fixed by blue-green algae. This group plays a key role in the nitrogen cycle but they are avoided in aquaculture systems because of their toxic compound production and off-flavour induction in fish flesh.

Organic matter in an aquatic environment results from excretion by organisms in it and death of these organisms. In aquaculture, the feed provided also adds organic matter to the water, either directly through uneaten feed or indirectly through increased excretion by the farmed organisms. This is especially so when large quantities of feed are added in intensive aquaculture methods. Decomposing organic matter releases nitrogenous compounds and carbon dioxide into the aquatic environment. Nitrogenous compounds in particular may reach undesirable levels or concentrations which are dangerous to the farmed organisms.

Phytoplankton and some species of bacteria are able to absorb nitrogenous compounds and/or convert them to less toxic or non-toxic forms. However, the assimilation of ammonia or nitrate by phytoplankton is low. Thus, in a traditional shrimp farming very low stocking densities are preferred to avoid any of the problems mentioned above. The inventors have found that surprisingly (We have not found that nitrifying bacteria maintain low ammonia and nitrates, it is a common knowledge in our field, but we can manipulate their growth (and nitrogen cycle too) by maintaining low concentration of nitrogenous compounds, by maintaining conditions to favour their growth, nitrifying bacteria are able to maintain nitrates in the aquatic environment at a low concentration to provide healthy conditions for the farmed organisms.

FIG. 1 shows the nitrogen cycle in an aquatic environment. Decomposing organic matter releases ammonia into the water upon ammonification, typically by both aerobic and anaerobic bacteria. Some naturally occurring anaerobic bacteria may be harmful and may grow to become dominant as organic matter in the water increases. Some of these bacteria may be pathogenic for the farmed organisms. However, some heterotrophic (aerobic and/or facultative anaerobic) bacteria are also able to break down organic matter into ammonia. While these bacteria may not be naturally present in large quantities, the inventors have found that, surprisingly, by adding sufficient quantities and maintaining conditions to favour their growth, these bacteria are able to displace the pathogenic bacteria and maintain healthy conditions for the farmed organisms. The ammonia generated by decomposing organic matter may next be removed by some bacteria such as *Nitrosomonas* and *Nitrobacter* which are respectively able to convert ammonia into nitrites, and nitrites into nitrates. Nitrates may be assimilated by phytoplankton but may also be undesirable if in quantities which are too large, as they may promote the growth of harmful phytoplankton such as blue-green algae. Denitrifying bacteria are thus important to convert nitrates into non-toxic nitrogen. The inventors have found that the method of the invention in manipulating these groups of organisms over the course of aquaculture production is surprisingly effective at maintaining good water quality even for high densities of farmed organisms. In particular, the method of the present invention manipulates groups of bacteria such as nitrifying, denitrifying and/or heterotrophic (aerobic and/or facultative anaerobic bacteria, such that sufficient populations of such bacteria grow in parallel with the increase in organic matter provided and therefore in parallel with the increase in the resulting nitrogenous compounds. These populations of bacteria are then able to work in synergy to maintain the concentration at a safe and desirable level for the healthy growth and development of the farmed organisms. In particular, the inventors found that by when the method of the present invention is used, nitrifying and heterotrophic (aerobic and facultative anaerobic) bacteria are able to work in synergy to reduce the concentration of nitrogenous compounds.

Accordingly, in some embodiments of the present invention, at least one of the phytoplankton allowed to grow, the added bacteria, and/or the bacteria allowed to grow may be capable of maintaining the concentration of ammonia and/or nitrites and/or nitrates in the aquatic environment at a level that is not toxic to the at least one farmed organism. Preferably, at least one of the added bacteria and/or the bacteria allowed to grow may be capable of maintaining the concentration of ammonia and/or nitrites and/or nitrates in the aquatic environment at a level that is not toxic to the at least one farmed organism.

In some embodiments of the present invention, the bacteria allowed to grow may comprise at least one species of nitrifiying bacteria.

In some embodiments of the present invention, at least one of the added bacteria and/or the bacteria allowed to grow may comprise at least one species of denitrifying bacteria.

In some embodiments of the present invention, at least one of the added bacteria and/or the bacteria allowed to grow may comprise at least one species of aerobic and/or facultative anaerobic bacteria.

Further, other nutrients such as magnesium, calcium, sodium and potassium are also crucial, and intensive production may also induce mineral deficiencies in water/soil due to the presence of limited amounts of these minerals in the pond. Uptake by the farmed organism to meet its requirements for healthy growth would thus diminish the availability of such essential minerals. The method of the present invention provides these essential minerals in a bioavailable form for the healthy growth of the farmed organism in intensive aquaculture. The provision of these essential minerals also helps to maintain a stable water environment.

Accordingly, in some embodiments of the present specification, the at least one phytoplankton nutrient provided comprises calcium, magnesium, potassium and sodium in forms and quantities suitable to grow phytoplankton that is not toxic or pathogenic to the at least one farmed organism.

The present invention relies on four concepts to manage organisms and their biochemical processes in the pond to balance the system:

Phytoplankton (N:P ratio):
N:P is the relationship between nitrogen and phosphorus concentration in the water. Phytoplankton groups are adapted to grow with different nitrogen and phosphorus requirements, and thus, by regulating this ratio the inventors are able to manage specific phytoplankton growth, without adding any phytoplankton to the water.
By controlling phytoplankton nutritional requirements, mainly nitrogen and phosphorus the growth of a specific phytoplankton group is promoted. Other important nutrients such as calcium, magnesium, potassium, sodium, etc. are also supplied.
These groups can be beneficial (green algae, diatoms) or harmful (blue green algae, dinoflagellata). The present invention balances N:P ratio, setting it around 16-20, promoting beneficial phytoplankton growth such as green algae and diatoms. This N:P ratio may not be optimal for some harmful phytoplankton such as blue-green algae, which may require a higher N:P ratio as can be seen from the below approximate guide:

| Type | N:P |
|---|---|
| nitrogen-fixing (Blue-Green) | 42-125 |
| Green | ~30 |
| Diatom | ~10 |
| Red Algae | ~10 |
| Dinophyceae | ~12 |

Beneficial phytoplankton growth stabilizes water quality (pH, temperature, nitrogenous compounds) and promotes natural food production, highly nutritious for shrimp.

Minerals:
The present invention provides dissolvable (bioavailable) forms of essential minerals and ions into the pond water for fish/shrimp to absorb directly from the water across gills, fins and other membranes. It will alleviate mineral deficiencies in the pond and shrimp, and it will balance acid-bases in the water.

Probiotics (C:N ratio):
Bacteria use nitrogen, organic matter, as energy source, thus reducing its concentration in the water and acting as bioremediator. To ensure a continuous bioremediation an external carbon source (molasses) is added to facilitate bacterial growth and performance. Amount of carbon source to be added is calculated depending on the water nitrogen concentration and ensuring a proper C:N ratio.

In the present invention, high performance probiotics (heterotrophic bacteria) are supplied to decompose organic matter in the water column and pond bottom, and nutrients and/or micronutrients are supplied that promote their growth. Aerobic and facultative anaerobic bacteria and micronutrients that effectively degrade organic matter in pond bottom even at low oxygen conditions.

In overall, bacterial activity reduces nitrogenous compounds toxicity and avoids anaerobic conditions that induce toxic hydrogen sulfide production. It helps recovering aerobic conditions after phytoplankton die-off (dead phytoplankton is organic matter that requires oxygen for its degradation), enhances nitrification reducing toxic nitrogenous compounds and promotes a clean bottom environment that allows higher benthic organisms.

Continuous probiotic addition suppresses pathogenic bacterial outbreak by out competing their growth in the water column, pond bottom and shrimp digestive tract.

ORP:

Nitrifying bacteria require aerobic conditions and essential nutrients to grow and perform. The present invention provides the nutrients for nitrifying bacteria and it facilitates a system with high ORP (Oxidation Reduction Potential) between +100 and +350 mV. A high value of ORP is related to oxidative, aerobic conditions, that favor nitrification, organic matter degradation and biological phosphorus removal.

Promoted aerobic conditions prevent hydrogen sulfide formation and undesirable fermentation in the pond bottom.

The present invention also provides the essential nutrients that promote nitrifying bacterial growth.

The present invention regulates above mentioned biochemical reactions and involved organisms to minimize toxic effects derived of high organic matter concentration in the water.

Nutrient supply ratios such as the ratio of nitrogen to phosphorous (N:P) or Carbon to nitrogen (C:N) are used in the method of the present invention to decide the amount of nutrients to provide, thus controlling the growth of phytoplankton and bacteria. These ratios refer to the desired relative atomic abundance of these elements and are understood by the skilled aquaculturist. As an example, Phosphorous and Nitrogen concentrations may be calculated with standard chemical methods, including all phosphorous-containing and nitrogenous compounds present in a sample of water taken from the aquatic environment. This is then compared to the desired N:P ratio and the appropriate amount of nitrogen- and/or phosphorous-containing phytoplankton nutrients may be provided. Similarly, the Carbon concentration needed to achieve a certain C:N ratio is calculated by multiplying the Nitrogen concentration with the C:N ratio, and the mass of Carbon source needed to achieve the Carbon concentration is calculated from the volume of aquatic environment used for aquaculture and the amount of bioavailable Carbon present in the Carbon source used. Carbon is typically used to promote the growth of bacteria, thus the Carbon source should provide carbon-containing compounds that are bioavailable to bacteria. Suitable Carbon sources may be any non-toxic Carbon-containing energy source such as molasses and jaggery, but not limited thereto. The skilled aquaculturist would be able to adjust the amount of Carbon source used according to the concentration of Carbon available in a unit of Carbon source.

Different N:P ratios may promote the growth of different groups of phytoplankton, and similarly different C:N ratios may promote the growth of different groups of bacteria. The inventors have found that the method of the present invention is surprisingly effective at promoting the growth of the desired groups of phytoplankton and bacteria by maintaining certain ranges of N:P and C:N ratios. N:P values as low as 10 induce harmful phytoplankton growth. Excessively high or low values induce harmful phytoplankton growth and the present invention balances it in around 16-20.

In particular, in some embodiments of the present invention, the at least one phytoplankton nutrient may be provided in an amount suitable for maintaining an N:P ratio in the aquatic environment between about 16 to about 20. Preferably, the N:P ratio may be maintained at this range across at least one predetermined period. More preferably, the N:P ratio may be maintained at this range across the first, second and third predetermined periods.

In some embodiments of the present invention, the at least one bacteria nutrient may be provided in an amount suitable for maintaining a C:N ratio in the aquatic environment suitable to grow bacteria that is not toxic to the at least one farmed organism. In some embodiments, the at least one bacteria nutrient may be provided in an amount suitable for maintaining a C:N ratio in the aquatic environment suitable to grow bacteria that is capable of maintaining the concentration of ammonia and/or nitrites and/or nitrates in the aquatic environment at a level that is not toxic to the at least one farmed organism. According to any of these embodiments, the C:N ratio may be between about 6 to about 10. Preferably, the C:N ratio may be maintained at this range across at least one predetermined period. More preferably, the C:N ratio may be maintained at this range across the first, second and third predetermined periods. According to any of these embodiments, the at least one bacteria nutrient provided may comprise at least one carbon source. Suitable carbon sources may be any non-toxic carbon source, such as molasses or jaggery, but not limited thereto.

In some embodiments of the present invention, the at least one bacteria nutrient is provided in an amount suitable for maintaining an Oxidation Reduction Potential (ORP) in the aquatic environment of between about +100 mV to about +350 mV. The inventors have found that this may help to promote the growth of the desired bacteria. In particular, maintaining the ORP in this range may enhance nitrification, reduce oxygen demand required for organic matter degradation and suppress hydrogen sulfide production.

In addition to the above bacteria nutrients, the desired groups of bacteria may require further nutrients in trace amounts for healthy growth. Accordingly, in some embodiments of the present invention, the at least one bacteria nutrient provided may comprise micronutrients in forms and quantities suitable to grow bacteria that is not toxic or pathogenic to the at least one farmed organism. In some embodiments the bacteria nutrient provided comprises micronutrients in forms and quantities suitable to grow bacteria that is capable of maintaining the concentration of ammonia and/or nitrites and/or nitrates in the aquatic environment at a level that is not toxic to the at least one farmed organism.

In some embodiments of the present invention, the aquatic environment may comprise the water phase and may also comprise the soil phase in a pond, and may further comprise any layer of organic matter and/or any cavity in fluid communication with the water phase.

The present invention may comprise of three phases which may correspond to the first, second and third predetermined periods. For example, some embodiments of the present invention may comprise the following phases:

Phytoplankton phase: (also referred to as first predetermined period)
Production stage: for example, Day Of Culture (DOC) 1 to DOC 35-40.
Organisms: photoautotrophic organisms (phytoplankton) are predominant.
Water quality: in the initial stages of production there is low organic matter content because feeding rates are not very high (small shrimp size and thus low feed amounts are added to the pond), having mainly inorganic matter.
Phytoplankton, which relies in inorganic matter to grow, is abundant due to water fertilization (supplied nitrogen, phosphorus and another essential nutrients), and it allows natural food growth. This natural food consists of zooplankton and other highly nutritious benthic organisms that provide additional food to shrimp, very important in the initial stage of production. Balanced phytoplankton population promotes a more stable environment, and thus water quality (pH, temperature, oxygen).

Phytoplankton and probiotic phase: (also referred to as second predetermined period)
Production stage: for example, DOC 35-40 to DOC 70-75.
Organisms: decreasing photoautotrophic (phytoplankton) organisms, and increasing chemoautotrophic (nitrifying bacteria) and heterotrophic bacteria.
Water quality: increase in organic matter content is proportional to feeding rates increase in the pond. Shrimp, larger in size, require more feed to grow and, therefore, produce more metabolic wastes (faeces, moulds, etc.) that added to increase in feeding rates, build up organic matter content of the water. Water environment, in turn, requires higher rates of organic matter degradation to ammonia by heterotrophic bacteria, and further nitrification to nitrites and nitrates by nitrifying bacteria. At this stage there is still phytoplankton abundance, but less important than in the previous stage.

Probiotic phase: also referred to as third predetermined period)
Production stage: for example, DOC 70-75 to harvest.
Organisms: chemoautotrophic (nitrifying bacteria) and heterotrophic bacteria are predominant.
Water quality: very high loads of organic matter (feed, faeces, moulds, etc) are decomposed by heterotrophic bacteria whilst nitrifying bacteria convert the resultant ammonia into inorganic nitrogen (nitrites and nitrates).

The above phases may also be represented in the following table that classifies the organisms by energy source:

| Energy Source | Autotrophic | Autotrophic and Heterotrophic | Autotrophic and Heterotrophic |
|---|---|---|---|
| DOC Phase | 1 to 35-40 Phytoplankton | 35-40 to 70-75 Phytoplankton and probiotic | 70-75 to harvest Phytoplankton and probiotic |
| Dominant organisms | Phytoplankton, zooplankton | Nitrifying and heterotrophic bacteria, phytoplankton (less) . . . | Nitrifying and heterotrophic |
| Obs. | Abundant natural food and low organic matter, mainly INORGANIC matter. | Increasing organic matter (feed), ammonia and urea. | High levels of ORGANIC matter, ammonia and urea. | matter.

An autotroph is an organism producing complex organic compounds from simple inorganic molecules using energy from light (phytoplankton) or inorganic chemical reactions (nitrifying bacteria). Some further examples include nitrifying bacteria like nitrosomonas *Nitrosomonas* spp. and *nitrobacter Nitrobacter* spp., denitrifying bacteria and blue-green algae.

An heterotroph is an organism that cannot fix carbon and uses organic carbon sources. Some examples are heterotrophic bacteria or probiotics, zooplankton and farmed organisms like shrimp.

Some organisms are defined as mixotrophs because they can perform as autotroph and heterotroph. Examples include some species of phytoplankton and zooplankton.

The present invention is described as a mixotrophic system because the system uses and manipulates both autotrophic (phytoplankton and nitrifying bacteria) and heterotrophic (bacteria) organisms throughout the production cycle.

Production cycle, from stocking to harvest, induces a succession from inorganic to organic compound abundance in water, which, in fact, is parallel to autotrophic (phytoplankton and nitrifying bacteria) to heterotrophic bacterial (probiotics) predominance throughout the above mentioned phases.

Surprisingly, the inventors have found that it is possible to manipulate groups of autotrophic and heterotrophic organisms to grow in synergy according to the method of the invention, allowing productivity of an aquaculture pond to be increased in a safe manner.

The present invention provides essential nutrients to promote phytoplankton, natural food and bacterial growth, stabilize water quality and ensure shrimp nutritional requirements fulfilment (supplied nutrients and promoted natural food growth). The present invention also provides beneficial bacteria (also known as probiotics) to the pond, that decompose organic matter and create a clean environment. These organisms activity balance biological (natural food, pathogens presence), physical (temperature) and chemical (oxygen, pH, organic matter, Nitrogen, etc.) parameters of the water allowing a higher and safer aquaculture production.

Phytoplankton, probiotic bacteria, their biochemistry and the benefits of applying them individually to aquaculture are known by the scientific community and aquaculture producers. Nevertheless, the method of the present invention provides a unique protocol to manage these factors in synergy, providing energy and nutrients to manage phytoplankton, bacteria and the water environment. The present invention promotes highly nutritional natural food (zooplankton, polichaetes, etc.) production and suppresses pathogens outbreak by controlling water, soil and microflora in the farmed organism, e.g. shrimp and fish. The invention thereby achieves surprising benefits such as:

Have an ecologically balanced system.
Minimize fluctuations of water and soil quality.
Reduce stress for the farmed organism.
Increase optimum carrying capacity.
Increases production by improving growth rate, FCR (Feed Conversion Rate), survival rate and daily growth of the farmed organism.
Reduces energy cost due to aeration management and zero water exchange.
Reduces feed and chemical compounds (such as lime, iodine) costs.
Manages pond soil and sediment.
Improves water and effluent quality and minimizes environmental impact.
Minimizes risk of failure due to disease or low production.
Long term sustainability of production.
All at economical cost and easy management.

The present invention balances water quality to avoid stress, disease outbreak or slow growth, and thus, increase productivity, health, growth and survival. All these benefits allow increasing production in a safe way and reducing feed and energy costs.

From the above, it may be seen that across the three predetermined periods that make up a production cycle, there may be an increase of organic matter concentration in the aquatic environment especially as increasing amounts of feed may be added. At the beginning of production in the first predetermined period, matter in the aquatic environment may be mainly inorganic. By the end of the third predetermined period, matter in the aquatic environment may be predominantly organic in nature. This shift from inorganic to organic matter may correspond to the shift from phytoplankton to bacterial predominance from the first predetermined period to the third predetermined period. Together with these shifts, there may also be a shift in the aquatic environment to substantially chemoautotrophic and heterotrophic organisms.

Accordingly, in some embodiments of the present invention, the third predetermined period, the at least one farmed organism, phytoplankton and bacteria present in the aquatic environment are substantially chemoautotrophic and heterotrophic.

As the method of the present invention uses and manipulates autotrophic (phytoplankton and nitrifying bacteria) and heterotrophic (bacteria) organisms throughout the production cycle to enhance the production quality and volume, the method of the present invention is known as a mixotrophic method of aquaculture or a mixotrophic system. Accordingly, for the purposes of this specification the method of the present invention may be interchangeably referred to as a "mixotrophic method of aquaculture" or a "mixotrophic system".

The method of the present invention is able to reduce the aeration needs of aquaculture production. For the purposes of the present invention, "aeration" refers primarily to the enrichment of the aquatic environment with oxygen and may also more generally comprise promoting gaseous exchange between a gas and the aquatic environment. For example, paddlewheel aerators are sometimes used in pond aquaculture to promote gaseous exchange between the pond water and the atmosphere, in the process removing carbon dioxide from the water and enriching the water with oxygen.

An "aerator" refers to any apparatus used to aerate the aquatic environment, and may be one or more than one units and types of aeration apparatus suitable for use alone or in combination in aquaculture. For example, the aerator may work by diffusion or by hydraulic action. A hydraulic aerator may comprise for example a cascade, a sprinkler, an ejector or an air intake head connected to a pump through a pipeline, or may comprise a surface aerator such as a simple open impeller or a centrifugal pump, placed at or near the surface of the aquatic environment to mix the water with the atmosphere. A diffusion type aeration apparatus may comprise for example a root-type blower, a ventilator, a compressor or a membrane pump to pump air into the aquatic environment through a porous material such as a perforated tube.

Examples of aerators include paddle aerators, cyclonic aerators, dissolved oxygen conditioners, Venturi oxygenators, fountain aerators, air injectors, pipe aerators, long arm aerators, circular aerators and cyclonic reducers are examples of aerators which are available commercially. Pure oxygen injection and oxygen diffusion systems are also increasingly used as aeration apparatus. These may have higher costs and may sometimes be reserved for use as emergency aerators to rapidly mitigate hypoxic conditions. Aerators may be used alone or in combination with other aerators to meet the oxygen demand from the organisms in the aquatic environment.

However, aerators may be energy intensive and/or expensive. Aquaculture production is often limited by the amount of aeration used to aerate the aquatic environment. For simplicity, the amount of aeration may be compared approximately across different farms in terms of the number of horsepower (hp) of aerators installed to aerate the aquatic environment and the number of hours the aerators are used per day. Alternatively, equivalents based on standard aerators such as a paddle aerator may be calculated by comparing the effective increase in oxygen content of the water.

The method of the present invention may also eliminate the need for water exchange in aquaculture. "Water exchange" refers to a common practice in aquaculture of draining or discharging water from the aquatic environment and replacing the discharged water with water of better quality, thereby improving the water quality of the aquatic environment. For example, in some aquaculture ponds beside a source of water such as a river, water of poor quality (for example, with low dissolved oxygen, high carbon dioxide and/or high nitrogenous compound concentration) may be discharged from the pond into the river downstream of the pond, and fresh water from upstream of the pond may be supplied to the pond, thereby improving the quality of water in the pond (higher dissolved oxygen, healthy concentrations of carbon dioxide and nitrogenous compounds). This cycle of discharging and replacing water, known as "water exchange," may also help to flush out excessive levels of phytoplankton, to reduce concentrations of nutrients, and to regulate salinity. It is energy intensive and may result in pollution of the natural water source with water of poor quality (having high carbon dioxide and nitrogenous compounds, and/or low oxygen). The method of the present invention does not comprise water exchange in that water exchange is not required to maintain or improve the quality of the aquatic exchange. More specifically, the method may not necessarily comprise the discharge of water from the aquatic environment during at least one of the first, second and/or third predetermined periods. However, normal inputs of water into the aquatic environment may be necessitated by excessive evaporation and/or seepage of water out of the pond through the walls of the pond, which may be in some instances water permeable. This replenishment of water lost may be required even with the method of the present invention.

Accordingly, in some embodiments of the present invention, the method may not comprise discharging water from the aquatic environment during at least one of the first, second and/or third predetermined periods. Preferably, the method may not comprise discharging water from the aquatic environment during any of the first, second and/or third predetermined periods.

The embodiments of the present invention are primarily concerned with a method of aquaculture of at least one farmed organism, wherein the farmed organism is not phytoplankton or bacteria. The at least one farmed organism may be selected from the group consisting of fish, crustaceans, molluscs, seaweeds and/or invertebrates. For example, the at least one farmed organism may be selected from the group consisting of Tilapias, Catfishes, Milkfishes, Groupers, Barramundi, Carps, Snakeheads, Catlas, Sturgeons, Eels, Mullets, Rohus, Seabasses, Seabreams, Rabbit fishes, Shrimps, Prawns, Crabs, Lobsters, Crayfishes, Oysters, Clams, Mussels, Scallops, Carpet shells, Abalones, Sea cucumbers, Sea urchins. In particular, the at least one farmed organism may be fish and/or shrimp.

In particular, the system of the present invention is particularly well suited for raising fish and/or shrimp. Thus, much of the remaining description may be directed to embodiments wherein the farmed organism is fish and/or shrimp. It should be understood, however, that the system is also well suited for raising other aquatic farmed organisms.

Aquaculture production may proceed via a production cycle, which may have a desired production cycle length depending on the desired end products of aquaculture. For example, the desired production cycle length may vary according to the species of farmed organisms and their growth requirements. The production cycle may start with the stocking of the aquatic environment with juvenile farmed organisms, for example with larval or postlarval shrimp. The production cycle may end with the harvest of the grown farmed organisms. However, grown farmed organisms are not necessarily fully mature. The desired production cycle length may also vary depending on the desired maturity of the farmed organisms at harvest.

In some embodiments, the method of the present invention may further comprise a step of determining a desired production cycle length for the at least one farmed organism, and the first predetermined period may be from about 30% to about 50% of the desired production cycle length and may begin with stocking of the aquatic environment;
the second predetermined period may be from about 30% to about 50% of the desired length of production cycle length, and may begin with the end of the first predetermined period and end with the start of the third predetermined period; and the third predetermined period may be from about 0% to about 40% of the desired production cycle length and may begin with the end of the second predetermined period and end with the harvesting of the at least one farmed organism.

In particular embodiments, the first predetermined period may be from about 30% to about 40% of the desired production cycle length and may begin with stocking of the aquatic environment;
the second predetermined period may be from about 30% to about 40% of the desired length of production cycle length, begin with the end of the first predetermined period and end with the start of the third predetermined period; and
the third predetermined period may be from about 30% to about 40% of the desired production cycle length, begin with the end of the second predetermined period and end with the harvesting of the at least one farmed organism. In some preferred embodiments, the three predetermined periods may be of equal length, i.e. each being a third of the production cycle.

In some embodiments, the method of the present invention may be directed to a method of aquaculture of at least one farmed organism wherein the at least one farmed organism comprises shrimp, the first predetermined period may be between about 35 to about 40 days, the second predetermined period may be between about 35 to about 40 days and the third predetermined period in the desired production cycle may be at least for about 5 days and may end with the harvest of the at least one farmed organism.

For the purposes of the present application, "Carrying capacity" refers to the amount (either expressed in weight or number) of farmed organisms that a given aquatic environment is capable of supporting. The carrying capacity is limited by a factor that on farms is usually oxygen then ammonia and carbon dioxide.

"Stocking density" refers to the weight or number of farmed organisms held per unit area or volume. Stocking densities depend on the farmed organism and its tolerance to the stress of increased overcrowding.

Accordingly, "stocking" for the purposes of this invention refers to introducing one or more organisms into the aquatic environment in working the invention. For example, the method of the invention may comprise an initial step of adding larvae or postlarvae of the farmed organism into the aquatic environment, which may already have phytoplankton and bacteria.

The stocking of the aquatic environment may be at a stocking density of a number of juvenile farmed organisms per unit volume or area of the aquatic environment. The unit area may be according to the area of the water surface. The present invention allows for a surprisingly high stocking density. For example, some embodiments of the present invention may be directed to a method of aquaculture of at least one farmed organism including shrimp, and may comprise a step of stocking at least about 200 shrimp per square meter of the aquatic environment at the start of the first predetermined period. In particular, some embodiments may comprise stocking at least about 300 shrimp per square meter of the aquatic environment at the start of the first predetermined period.

Feed conversion ratio or "FCR" refers to the ratio between the dry weight of feed fed to the farmed organisms to allow them to grow and the weight gain by the farmed organisms after growth. FCR is a measure of the efficiency of conversion of feed to fish—for example, a FCR of 2.8 means that 2.8 kg of feed is needed to produce 1 kg of fish live weight). Different species of farmed organisms have different FCR depending on the method of aquaculture used. For example, Tilapia may have a typical FCR or 1.6 to 1.8. Typical shrimp faming may have a FCR of above about 1.5. As may be seen from the data provided below, the inventors have surprisingly found that by using the method of the present invention, an average FCR of 1.29 is obtained for shrimp farming, as compared to an average FCR of 1.59 when using traditional methods. This means that the increase in mass for the farmed shrimp from stocking to harvest was on average 0.775 times the mass of the cumulative feed provided, compared to just 0.629 times when using traditional methods. However, the present invention is not limited to embodiments such as these. The same effect of improving the FOR applies to all farmed organisms. Values may differ, but there is always a clear improvement.

Accordingly, in some embodiments of the present invention, the use of the method of the present invention to allow the farmed organisms to grow may increase the mass of the farmed organisms by at least about 0.7 times the mass of the at least one additional feed provided from the start of the first predetermined period to the end of the third predetermined period.

With traditional farming techniques, stocking density is limited by the abovementioned problems. For example, in shrimp farming it is impossible to reach a stocking density of 300-400 postlarvae (PL) per square meter of the farm surface in a sustainable way, as such a high stocking density would induce an unstable system prone to failure and disease.

Surprisingly, the inventors have found that using the method of the present invention to manipulate the aquatic environment (managing the water and soil quality) allows a much higher stocking density in aquaculture. The inventors have manipulated phytoplankton and bacterial activity to balance the system and increase production safely.

As may be seen from the below data on production performance improvement comparing traditional aquaculture methods and the method of the present invention, the benefits of using the present invention include: increased stocking density, increased growth rate, increased production, reduced FCR, reduced (or improved) aeration costs, etc. all in a sustainable way.

Further, the present invention is unique and inventive in providing a complete protocol adapted to any species, or farm particularities to manage the pond environment throughout the culture cycle to increase production rates minimizing disease outbreaks at stocking densities much higher than in general aquaculture practise, and at reduced costs.

For example, in important shrimp farming countries such as Thailand, India or Ecuador, prior art methods achieve a stocking density of 200, 100 and 30 postlarvae per square meter, respectively. With the present invention more than 200 and typically about 300 to about 400 postlarvae per square meter may be stocked.

Traditional aquaculture farming methods may comprise aquatic environments with phytoplankton and bacterial populations. However, there is no protocol to manipulate the activity of phytoplankton and bacteria populations. Accordingly, a skilled aquaculturist would not expect to control these organisms, phytoplankton and bacteria, their biochemistry and thus, manipulate them to enhance the quality and volume of aquaculture production. This disclosure provides a novel and inventive method of aquaculture comprising a protocol that can manipulate these populations of organisms by regulating the energy and nutrients that these organisms obtain from the water.

In another aspect of the present invention, there is provided an aquaculture system capable of performing the method according to any aspect of the present invention, the system comprising:
(A) an aquatic environment comprising at least one farmed organism, phytoplankton and bacteria, and/or means to provide such an environment;
(B) at least one phytoplankton nutrient providing means for providing at least one phytoplankton nutrient to the aquatic environment;
(C) at least one phytoplankton nutrient sensing means for sensing at least one phytoplankton nutrient concentration in the aquatic environment;
(D) at least one bacteria nutrient providing means for providing at least one bacteria nutrient to the aquatic environment;
(E) at least one bacteria adding means for adding at least one bacteria to the aquatic environment; and
(F) at least one bacteria nutrient sensing means for sensing at least one bacteria nutrient concentration in the aquatic environment.

To provide the appropriate amount of nutrients and/or bacteria, and/or to maintain the nutrients and/or bacteria at a certain concentration, an aquaculture system may be used that may comprise various sensing means operatively coupled to various providing means. For example, sensors or testing apparatus to determine concentrations of substances and/or organisms in the water, that may indicate when further nutrient and/or bacteria should be provided to the water. The system may be manual, automated or partially automated, for instance it may comprise an automatic nutrient dispenser device and/or automated sampling systems and sensing systems, such as those available at http://www.aquacultureequipment.co.uk and/or http://www.campbellsci.com.au/products and/or http://www.ysi.com/products.php. However, the invention is not limited to such embodiments, and includes embodiments where all or part of the features of the aquaculture system rely on human operators.

In some embodiments of the present invention, the aquaculture system may further comprise:
(G) at least one phytoplankton nutrient maintaining means operatively coupled to at least one phytoplankton nutrient providing means and/or at least one phytoplankton nutrient sensing means to maintain the phytoplankton nutrient at a concentration suitable to grow phytoplankton; and
(H) at least one bacteria nutrient concentration maintaining means operatively coupled to at least one bacteria nutrient providing means and/or at least one bacteria nutrient sensing means to maintain the bacteria nutrient at a concentration suitable to grow bacteria, wherein the phytoplankton and bacteria are allowed to grow in a phytoplankton:bacteria ratio of more than 1 during the first predetermined period; the phytoplankton and bacteria are allowed to grow in a second predetermined phytoplankton:bacteria ratio during the second predetermined period, wherein the second predetermined phytoplankton:bacteria ratio is lower than the first predetermined phytoplankton:bacteria ratio; and the phytoplankton and bacteria are allowed to grow in a third predetermined phytoplankton:bacteria ratio during the third predetermined period,
wherein the third predetermined phytoplankton:bacteria ratio is lower than the second predetermined phytoplankton:bacteria ratio.

There may be some instances where excessive growth of even the desired phytoplankton and bacteria may induce low oxygen-derived harmful situations. Accordingly, in some embodiments of the present invention, the aquaculture system may further comprise:
(I) at least one phytoplankton sensing means for sensing the concentration of the phytoplankton allowed to grow;
(J) at least one bacteria sensing means for sensing the concentration of the bacteria allowed to grow;
(K) at least one phytoplankton nutrient concentration maintaining means operatively coupled to at least one phytoplankton nutrient providing means and/or at least one phytoplankton sensing means to prevent further provision of phytoplankton nutrient when the concentration of the phytoplankton allowed to grow reaches a first predetermined concentration, until the concentration of the phytoplankton allowed to grow falls below the first predetermined concentration; and (L) at least one bacteria nutrient concentration maintaining means operatively coupled to at least one bacteria nutrient providing means and/or at least one bacteria sensing means to prevent further provision of bacteria nutrient and/or further adding of bacteria when the concentration of the bacteria allowed to grow reaches a second predetermined concentration, until the concentration of the bacteria allowed to grow falls below the second predetermined concentration. The first and second predetermined concentrations may indicate excessive growth of phytoplankton and bacteria respectively.

Bacteria sensing means and phytoplankton sensing means may comprise manual investigation of water samples in a laboratory and/or apparatus that are able to count and/or identify bacteria and/or phytoplankton. For example, bacteria sensing means may comprise a genetic analysis device such as the one envisioned in http://www.springerlink.com/content/v5443m2823833888/. However, in most cases the use of such devices may not presently be possible on a wide scale due to cost reasons.

In common aquaculture practice, phytoplankton and bacteria populations may not be measured directly by apparatus for counting the concentrations of the phytoplankton and bacteria. Instead, indirect means may be used to indicate excessive growth of the phytoplankton and/or bacteria. For example, in some embodiments of the present invention, the aquaculture system may further comprise apparatus for obtaining a Secchi disk visibility reading for the aquatic environment, and the phytoplankton nutrient providing means may provide no further phytoplankton nutrient when the aquatic environment Secchi disk visibility is less than about 30 cm, and may resume providing phytoplankton nutrient when the aquatic environment Secchi disk visibility increases to more than about 30 cm.

Low dissolved oxygen levels in the aquatic environment may also signal a need to stop providing further bacteria nutrient. Accordingly, in some embodiments of the present invention, the at least one bacteria sensing means may comprise an apparatus for measuring dissolved oxygen in the aquatic environment, and the bacteria nutrient providing means may provide no further bacteria nutrient when the dissolved oxygen in the aquatic environment is less than about 3.5 mg/L, and may resume providing bacteria nutrient when the dissolved oxygen in the aquatic environment increases to more than about 3.5 mg/L. Similarly, other environmental parameters may indicate a need to stop, increase or decrease amounts of feed and/or phytoplankton and/or bacteria nutrients provided. Sensors suitable for sensing these parameters are for example found at http://www.ysi.com/products.php, http://www.aquacultureequipment.co.uk and/or http://www.campbellsci.com.au/products.

Example 1

Production Performance and Water Quality Data Records

The following table summarizes the difference in aquaculture production performance between a traditional shrimp farming system and a shrimp farm using the method of the present invention.

TABLE 1

| | Traditional | Mixotrophic | Improvement (%) |
|---|---|---|---|
| Stocking density (PL/sqm) | 85 | 209 | 146 |
| Average Body Weight (g) | 13.62 | 14.34 | 5 |
| ADGR (g/day) | 0.16 | 0.20 | 26 |
| Survival (%) | 65.6 | 81.6 | 24 |
| FCR | 1.59 | 1.29 | 19 |
| kg harvested/hp | 266 | 677.68 | 155 |
| kg feed day/hp | 4.90 | 12.29 | 151 |

*hp = horsepower installed in the pond.

More detailed data tables follow after the below discussion of the results.

Increase in stocking density allows harvesting more shrimp volume without affecting survival rate. The data shows that there is even an improvement in survival rate and more shrimp volume can be harvested per horsepower aerator installed (=energy saving) when the method of the present invention is implemented.

Aeration management is improved in that more shrimp volume may be produced with the same aeration in a safe manner or the amount of aeration installed (hp) may be reduced to produce the same volume and, thus, energy costs are lowered.

More feed volume (kg) can be given with the method of the present invention per horsepower installed. It means that the system is balanced and more organic matter is allowed in the system without affecting shrimp health, because we are maintaining a good water quality. Average body weight is also larger in less culture days.

There is a decrease in FCR and an increase in average daily growth rate (g/day) because the water quality is not slowing shrimp growth. Healthy shrimp will metabolize feed better and therefore, they will grow much better, improving feed conversion rate (FCR).

Water and soil quality management is an important part of farming, therefore, water quality data are also shown to provide a view of the system management.

PONDS E5, E6, E7 and E8 (Traditional Shrimp Farming System)

pH is a logarithmic function what means that a unit increase or decrease is a tenfold change. Therefore, unstable pH (as the one shown in the data for the traditional shrimp farm) during the production cycle leads to shrimp stress, thus decrease in productivity and it may induce disease outbreak.

Ammonia peaks as shown in the data cause stress to shrimp reducing productivity and leading to disease outbreak.

Organic matter increase should be gradual. Sudden increases as in ponds E5 and E6 are due to unbalanced system where organic matter is accumulated and this requires high oxygen demand. Anaerobic zones may be created leading to toxic gas formation with all the harmful effects on shrimp health.

PONDS D1, D6, D10, D4 and D5 (Mixotrophic Shrimp Farming System)

Stable pH is a sign of balanced phytoplankton activity and acid-base concentration.

The data shows how ammonia is maintained always at low levels, due to continuous nitrification and phytoplankton ammonia removal. Nitrite gradually increases paralelly to organic matter increase from stocking to harvest. Ammonia levels close to cero do not mean that there is not ammonia, but this is due to the ammonia measurement method that gives a result of ammonia, close to zero (in the tables as well ammonia values of zero, do not mean there is not ammonia, but that there is a low concentration). Ammonia is necessary al the time for nitrifying bacteria to grow and convert it to nitrite and nitrates.

Decrease in Secchi disk visibility is related to phytoplankton bloom at the beginning of stocking. Then, it slowly stabilizes, whilst organic matter slightly accumulates due to increased volume of feed.

The following tables provide more detailed data on aquaculture production performance (Total Production (=harvested kg), FCR, Survival Rate (SR, %), "daily feed vs. installed horsepower" and "total amount of feed given vs. installed horsepower") and water quality in a traditional shrimp farming system and in a shrimp farm using the method of the present invention.

TABLE 2

Shrimp farming (traditional), PRODUCTION DATA AND INDICATORS

| Pond | Date stocked | Pond size (sqm) | DOC | Density (PL/sqm) | Total stocked (pcs) | Average Body Weight (g) | ADGR (g/day) | Survival (%) |
|---|---|---|---|---|---|---|---|---|
| E5 | 6 Feb. 2011 | 4700 | 83 | 85 | 399000 | 15.33 | 0.18 | 52.4 |
| E6 | 4 Feb. 2011 | 4000 | 88 | 84 | 336600 | 15.95 | 0.18 | 78.0 |
| E7 | 6 Feb. 2011 | 4100 | 87 | 85 | 346500 | 15.98 | 0.18 | 57.0 |
| E8 | 3 Feb. 2011 | 4000 | 81 | 86 | 342700 | 7.21 | 0.09 | 75.0 |
| Average | | | | 85 | | 13.62 | 0.16 | 65.6 |

| Pond | Date stocked | FCR | Total feed (kg) | Average Daily Feed (kg) | Harvest Biomass (kg) | Horsepower (hp) installed | kg harvested/ hp | kg feed day/hp |
|---|---|---|---|---|---|---|---|---|
| E5 | 6 Feb. 2011 | 1.79 | 5737.0 | 69.1 | 3205.0 | 14 | 229 | 4.94 |
| E6 | 4 Feb. 2011 | 1.35 | 5651.7 | 64.2 | 4186.5 | 11 | 381 | 5.84 |
| E7 | 6 Feb. 2011 | 1.77 | 5585.4 | 64.2 | 3155.6 | 11 | 287 | 5.84 |
| E8 | 3 Feb. 2011 | 1.44 | 2669.1 | 33.0 | 1853.6 | 11 | 169 | 3.00 |
| Average | | 1.59 | | | | | 266 | 4.90 |

TABLE 3

Blue Aqua's Mixotrophic System for Intensive Shrimp Farming, PRODUCTION DATA AND INDICATORS

| Pond | Date stocked | Pond size (sqm) | DOC | Density (PL/sqm) | Total stocked (pcs) | Average Body Weight (g) | ADGR (g/day) | Survival (%) |
|---|---|---|---|---|---|---|---|---|
| D1 | 11 Dec. 2011 | 3400 | 71 | 214 | 727800 | 14.21 | 0.20 | 95.1 |
| D2 | 11 Dec. 2011 | 3900 | 72 | 202 | 788800 | 14.14 | 0.20 | 89.0 |
| D6 | 11 Dec. 2011 | 5300 | 74 | 206 | 1089400 | 14.83 | 0.20 | 87.3 |
| D9 | 11 Dec. 2011 | 4300 | 69 | 196 | 841900 | 13.45 | 0.19 | 72.2 |
| D10 | 11 Dec. 2011 | 3700 | 70 | 208 | 771300 | 15.53 | 0.22 | 84.6 |
| D7 | 14 Dec. 2011 | 5000 | 71 | 194 | 971000 | 15.12 | 0.21 | 67.7 |
| D4 | 16 Dec. 2011 | 5900 | 72 | 222 | 1310000 | 14.22 | 0.20 | 81.5 |
| D3 | 17 Dec. 2011 | 5100 | 71 | 220 | 1124400 | 14.24 | 0.20 | 64.6 |
| D5 | 17 Dec. 2011 | 5000 | 70 | 208 | 1038800 | 14.20 | 0.20 | 78.0 |
| D8 | 22 Dec. 2011 | 4700 | 71 | 217 | 1020200 | 13.46 | 0.19 | 96.2 |
| Average | | | | 209 | | 14.34 | 0.20 | 81.6 |

TABLE 4

Blue Aqua's Mixotrophic System for Intensive Shrimp Farming, PRODUCTION DATA AND INDICATORS

| Pond | Date stocked | Pond size (sqm) | DOC | FCR | Total feed (kg) | Average Feed/ day (kg) | Harvest Biomass (kg) | Horsepower (hp) installed | kg harvested/ hp installed | Daily feed (kg)/hp |
|---|---|---|---|---|---|---|---|---|---|---|
| D1 | 11 Dec. 2011 | 3400 | 71 | 1.25 | 12300.0 | 173.2 | 9837.3 | 16 | 615 | 10.83 |
| D2 | 11 Dec. 2011 | 3900 | 72 | 1.24 | 12345.3 | 171.5 | 9922.5 | 16 | 620 | 10.72 |
| D6 | 11 Dec. 2011 | 5300 | 74 | 1.23 | 17326.0 | 234.1 | 14109.2 | 20 | 705 | 11.71 |
| D9 | 11 Dec. 2011 | 4300 | 69 | 1.37 | 11197.0 | 162.3 | 8172.3 | 12 | 681 | 13.52 |
| D10 | 11 Dec. 2011 | 3700 | 70 | 1.20 | 12135.0 | 173.4 | 10139.1 | 16 | 634 | 10.83 |
| D7 | 14 Dec. 2011 | 5000 | 71 | 1.40 | 13935.0 | 196.3 | 9937.8 | 15 | 663 | 13.08 |
| D4 | 16 Dec. 2011 | 5900 | 72 | 1.29 | 19534.0 | 271.3 | 15179.2 | 20 | 759 | 13.57 |

TABLE 4-continued

Blue Aqua's Mixotrophic System for Intensive
Shrimp Farming, PRODUCTION DATA AND INDICATORS

| Pond | Date stocked | Pond size (sqm) | DOC | FCR | Total feed (kg) | Average Feed/ day (kg) | Harvest Biomass (kg) | Horse-power (hp) installed | kg harvested/ hp installed | Daily feed (kg)/hp |
|---|---|---|---|---|---|---|---|---|---|---|
| D3 | 17 Dec. 2011 | 5100 | 71 | 1.46 | 15163.0 | 213.6 | 10351.2 | 16 | 647 | 13.35 |
| D5 | 17 Dec. 2011 | 5000 | 70 | 1.32 | 15142.0 | 216.3 | 11512.9 | 16 | 720 | 13.52 |
| D8 | 22 Dec. 2011 | 4700 | 71 | 1.14 | 15016.0 | 211.5 | 13206.0 | 18 | 734 | 11.75 |
| Average | | | | 1.29 | | | | | 677.68 | 12.29 |

TABLE 5

Shrimp farming (traditional technique), WATER QUALITY

| | DOC (day) | 7 | 14 | 21 | 28 | 35 | 42 | 49 | 56 | 63 | 70 | 77 | 84 |
|---|---|---|---|---|---|---|---|---|---|---|---|---|---|
| Pond E5 | pH | 7.7 | 8.2 | 8.4 | 8.3 | 8.3 | 8.3 | 7.9 | 8.1 | 7.9 | 7.9 | 7.7 | |
| | Ammonia (ppm) | 0 | 0 | 0 | 0 | 0 | 0.5 | 0 | 0 | 0 | 0 | 0 | |
| | Nitrite (ppm) | 0.05 | 0.05 | 0.1 | 0.05 | 0.05 | 0.05 | 0.05 | 0.05 | 0.05 | 0 | 0.05 | |
| | Organic matter (g) | 48.2 | 13.4 | 17.3 | 17.9 | 14.7 | 21.2 | 29.7 | 29.3 | 24.8 | 37.2 | 43.4 | |
| Pond E6 | pH | 7.9 | 8.2 | 8.2 | 8.3 | 7.9 | 8.1 | 8.3 | 8.3 | 7.9 | 8.2 | 8.2 | 8.1 |
| | Ammonia (ppm) | 0 | 0 | 0 | 0 | 0 | 0 | 0 | 0.5 | 0 | 0 | 0.5 | 0 |
| | Nitrite (ppm) | 0.05 | 0.05 | 0.05 | 0.05 | 0.05 | 0.05 | 0.05 | 0.05 | 0 | 0 | 0.05 | 0 |
| | Organic matter (g) | 5.5 | 17.3 | 26.4 | 22.2 | 35.4 | 20.5 | 28.4 | 27.1 | 28.7 | 32.3 | | 35.9 |
| Pond E7 | pH | 8.1 | 7.7 | 8.3 | 8.2 | 8 | 8.2 | 7.9 | 8.1 | 7.9 | 7.8 | 8 | 7.9 |
| | Ammonia (ppm) | 0 | 0 | 0 | 0 | 0 | 0 | 0 | 0 | 0.5 | 0 | 0.5 | 1 |
| | Nitrite (ppm) | 0.05 | 0.05 | 0.05 | 0.05 | 0.05 | 0.05 | 0.05 | 0.05 | 0 | 0.05 | 0.6 | 1 |
| | Organic matter (g) | 18.9 | 25.4 | 19.9 | 18.3 | 21.8 | 28.4 | 28.7 | 29 | 30.3 | 35.5 | 43.8 | 37.9 |
| Pond E8 | pH | 7.9 | 8 | 8.2 | 7.9 | 8 | 8.2 | 8.2 | 8.1 | 7.9 | 7.8 | 7.9 | |
| | Ammonia (ppm) | 0 | 0 | 0 | 0 | 0 | 0 | 0 | 0 | 0 | 0.5 | 0.5 | |
| | Nitrite (ppm) | 0.05 | 0.05 | 0.05 | 0.05 | 0.05 | 0 | 0.05 | 0.05 | 0.1 | 1 | 1 | |
| | Organic matter (g) | 17.3 | 24.5 | 19.6 | 19.6 | 26.1 | 23.8 | 25.4 | 29.7 | 35.2 | 42.8 | 47 | |

TABLE 6

| | DOC | Secchi disk (cm) | pH | Ammonia (ppm) | Nitrite (ppm) | Organic matter (g) |
|---|---|---|---|---|---|---|
| Pond D1 | 7 | 100 | 7.8 | 0 | 0.1 | 77.1 |
| | 14 | 100 | 7.9 | 0.5 | 0.1 | 61.9 |
| | 21 | 85 | 8 | 0 | 0.05 | 98.6 |
| | 28 | 70 | 7.9 | 0 | 0.05 | 90.1 |
| | 35 | 55 | 7.9 | 0 | 0.2 | 99.9 |
| | 42 | 45 | 7.8 | 0 | 0.2 | 111.2 |
| | 49 | 45 | 7.6 | 0 | 1 | 107.4 |
| | 56 | 40 | 7.8 | 0.5 | 1.8 | 108.7 |
| | 63 | 35 | 7.7 | 1 | 1 | 106.2 |
| | 70 | 30 | 7.6 | 2 | 3 | 102.3 |
| Pond D6 | 14 | 100 | 8.2 | 0 | 0.05 | 108.7 |
| | 21 | 90 | 8 | 0 | 0.05 | 68.2 |
| | 28 | 75 | 7.9 | 0 | 0.05 | 97.3 |
| | 35 | 60 | 7.9 | 0 | 0.05 | 106.2 |
| | 42 | 40 | 7.7 | 0 | 0.05 | 108.7 |
| | 49 | 35 | 7.8 | 0 | 0.4 | 99.9 |
| | 56 | 30 | 7.8 | 0 | 1 | 108.7 |
| | 63 | 25 | 7.7 | 0 | 6 | 113.8 |
| | 70 | 30 | 7.6 | 0 | 6 | 111.2 |
| | 77 | 30 | 7.7 | 0 | 10 | 92.3 |
| Pond D10 | 14 | 100 | 8.1 | 0 | 0.05 | 106.2 |
| | 21 | 75 | 8.2 | 0 | 0 | 64.5 |
| | 28 | 50 | 7.9 | 0 | 0.05 | 109.9 |
| | 35 | 35 | 8 | 0 | 0.05 | 99.9 |
| | 42 | 30 | 7.8 | 0 | 0.05 | |
| | 49 | 30 | 7.8 | 0 | 0.4 | 106.2 |
| | 56 | 30 | 7.8 | 0 | 1 | |
| | 63 | 30 | 7.7 | 0 | 3 | 112.5 |
| | 70 | 30 | 7.7 | 0 | 10 | 109.9 |
| | 77 | 30 | 7.7 | 0 | 10 | 86 |
| Pond D4 | 7 | 100 | 7.9 | 0 | 0.05 | 60.7 |
| | 14 | 100 | 8.2 | 0 | 0.05 | 101.1 |
| | 21 | 85 | 8.1 | 0 | 0.05 | 54.4 |
| | 28 | 65 | 7.8 | 0 | 0.05 | 96.1 |
| | 35 | 40 | 7.8 | 0 | 0.1 | 104.9 |
| | 42 | 30 | 7.8 | 0 | 0.2 | 111.2 |
| | 49 | 30 | 7.8 | 0 | 0.6 | 103.6 |
| | 56 | 30 | 7.7 | 0 | 1 | 108.7 |
| | 63 | 30 | 7.7 | 0 | 6 | 107.4 |
| | 70 | 25 | 7.7 | 0 | 6 | 109.9 |
| | 77 | 25 | 7.6 | 0 | 10 | 96.1 |
| Pond D5 | 7 | 100 | 7.9 | 0 | 0.05 | 60.7 |
| | 14 | 100 | 8.1 | 0 | 0.05 | 65.7 |
| | 21 | 100 | 8 | 0 | 0.05 | 79.6 |
| | 28 | 85 | 7.8 | 0 | 0.05 | 72 |
| | 35 | 70 | 7.8 | 0 | 0.05 | 87.2 |
| | 42 | 50 | 7.8 | 0 | 0.05 | 79.6 |
| | 49 | 30 | 7.7 | 0 | 0.05 | 96.1 |
| | 56 | 30 | 7.6 | 0 | 0.2 | 88.5 |
| | 63 | 30 | 7.6 | 0 | 1 | 89.7 |
| | 70 | 30 | 7.7 | 0 | 6 | 102.4 |

Example 2

Economic Analysis of a 3.1 MT Shrimp Production on a Farm Using a Conventional Shrimp Farming Method Compared with an Equivalent Farm Using the (Mixotrophic) Method of the Present Invention General Information Production volume equals to 3.1 MT.
Feed cost equals to 1.24 SGD/kg.
FCR=1.59 vs. 1.29 (Conventional vs. Mixotrophic).

85 Days Of Culture (DOC).

Total pond area equals to 1.6 ha.

Liming Information:

Application 3×/week at 200 kg/ha.

Lime cost is 0.124 SGD/kg. (Mixotrophic System does not use lime).

Traditional aquaculture methods often include a step of applying various acid-neutralizing compounds of calcium or calcium and magnesium to the aquaculture pond, for example before filling it with water. This is known as "liming" and has three important benefits: 1) Liming may enhance the effect of fertilization. 2) Liming helps prevent wide swings in pH. 3) Liming also adds calcium and magnesium, which are important in the proper development of a farmed organism. Materials such as agricultural limestone, basic slag, slaked lime, quick lime and liquid lime have been used to lime ponds. Liming materials may comprise one or more of the carbonate, hydrogen carbonate, hydroxide, and oxide salts of calcium and magnesium. However, as can be seen from the above data, multiple applications are usually required and can be expensive. The present invention allows lower costs of aquaculture pond operation by balancing the pH and manipulating the environment such that liming is not required.

Energy Costs Information:

Energy cost 0.124 SGD/kWh.

Aeration:

Hours of operation/day=8

Days of operation=85

Motor efficiency 80% in both cases.

Conventional system: 12 hp installed (266 kg/hp; from performance table))

Mixotrophic System: 5 hp installed (677 kg/hp; from performance table)).

Pumping 2 hp pump of 80% efficiency in both cases.

Hours operation/day=4 (Conventional System).

Hours operation/day=0.5 (Mixotrophic System, Zero Water Exchange, only evaporation replenishment).

Aeration and water exchange are also significant contributors to energy costs for aquaculture production, especially in aquaculture locations where energy costs are high. The method of the present invention manipulates the environment such that much there are lower aeration requirements for a given amount of production. The above data shows the improvement in performance (expressed as "shrimp volume (kg) harvested per installed horsepower" and "daily feed volume (kg) per installed horsepower") when a traditional shrimp farm adopts the method of the present invention. By this data it may be seen that using the same installed horsepower of aerators, we can three-fold the production volume from 266 to 677 kg per installed horsepower.

Water exchange is also not required in the method of the present invention, although water evaporated from the aquatic environment should be replenished. Further energy and operational cost savings are thus realised from not having to operate water pumps to drain or discharge water from the aquaculture ponds, and having to refill the drained aquaculture ponds before proceeding with the next stage of aquaculture.

Figure 2:
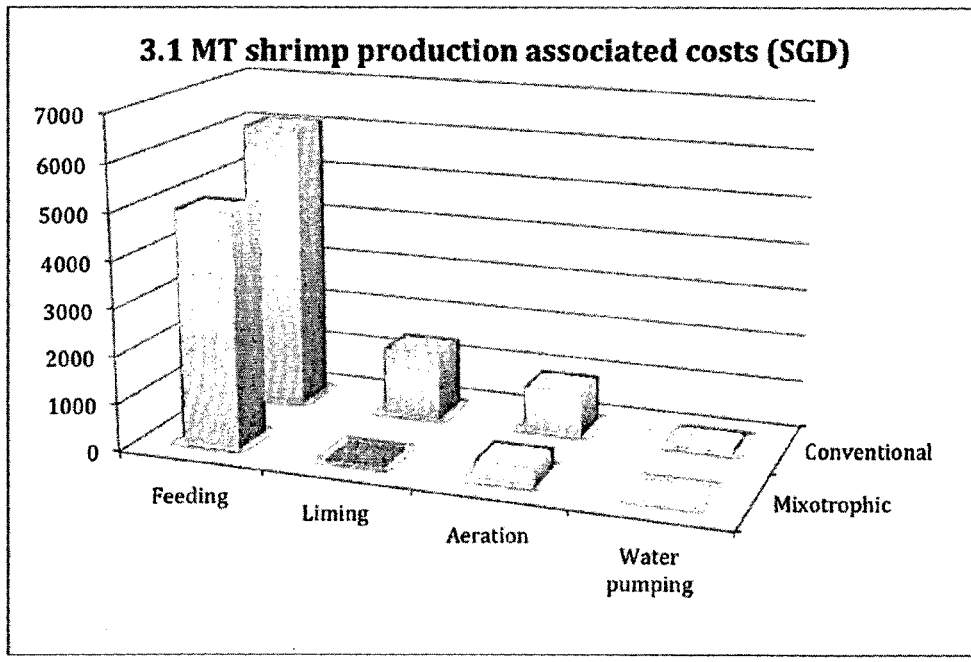
FIG. 2 is a bar chart showing the results of the Economic Analysis done in Example 2 to compare shrimp farming using a traditional aquaculture method and the method of the present invention.

The costs of production for the respective farms are compared in FIG. 2, showing that lower costs in feeding, liming, aeration and water exchange/water pumping lead to a total savings of approximately SGD 3232 for 3.1 MT of shrimp.

The subject matter claimed herein is not limited to embodiments that solve any disadvantages or that operate only in environments such as those described above. Rather, this background is only provided to illustrate on exemplary technology area where some embodiments described herein may be practiced. Bibliographic references mentioned in the present specification are for convenience listed in the form of a list of references and added at the end of the examples. The whole content of such bibliographic references is herein incorporated by reference.

The invention claimed is:

1. A method of aquaculture of at least one farmed organism, the method comprising steps:
   (i) supplying an aquatic environment comprising at least one farmed organism, phytoplankton and bacteria;
   (ii) supplying at least one phytoplankton nutrient and at least one bacteria nutrient during a first predetermined period, allowing phytoplankton and bacteria to grow in a first predetermined phytoplankton:bacteria ratio of at least 60:40;
   (iii) supplying at least one phytoplankton nutrient and at least one bacteria nutrient during a second predetermined period, allowing phytoplankton and bacteria to grow in a second predetermined phytoplankton:bacteria ratio, wherein the second predetermined phytoplankton:bacteria ratio is lower than the first predetermined phytoplankton:bacteria ratio and wherein the second predetermined phytoplankton:bacteria ratio is between 75:25 to 25:75; and
   (iv) supplying at least one phytoplankton nutrient and at least one bacteria nutrient during a third predetermined period, allowing phytoplankton and bacteria to grow in a third predetermined phytoplankton:bacteria ratio, wherein the third predetermined phytoplankton:bacteria ratio is lower than the second predetermined phytoplankton:bacteria ratio, and wherein the third predetermined phytoplankton:bacteria ratio is less than 40:60,
   thereby allowing the at least one farmed organism to grow.

2. The method according to claim 1, wherein the at least one phytoplankton nutrient and at least one bacteria nutrient are supplied during the first, second and third predetermined periods at respective concentrations suitable to grow phytoplankton and bacteria in the first, second and third predetermined phytoplankton:bacteria ratios.

3. The method according to claim 1, wherein the at least one phytoplankton nutrient is supplied during the first, second and third predetermined periods in decreasing concentrations suitable to grow phytoplankton and bacteria in the first, second and third predetermined phytoplankton:bacteria ratios.

4. The method according to claim 1, wherein the at least one bacteria nutrient is supplied during the first, second and third predetermined periods in increasing concentrations suitable to grow phytoplankton and bacteria in the first, second and third predetermined phytoplankton:bacteria ratios.

5. The method according to claim 1, further comprising adding bacteria to the aquatic environment, wherein the added bacteria is capable of maintaining the concentration of ammonia and/or nitrites and/or nitrates in the aquatic environment at a level that is not toxic to the at least one farmed organism and/or wherein the bacteria is not toxic or pathogenic to the at least one farmed organism.

6. The method according to claim 5, wherein the bacteria is added during the first, second and third predetermined periods in increasing concentrations suitable to allow phytoplankton and bacteria to grow in the first, second and third predetermined phytoplankton:bacteria ratios.

7. The method according to claim 1, wherein the first predetermined phytoplankton:bacteria ratio is at least 75:25.

8. The method according to claim 1, wherein the first predetermined phytoplankton:bacteria ratio is at least 90:10.

9. The method according to claim 1, wherein the second predetermined phytoplankton:bacteria ratio is between 60:40 to 40:60.

10. The method according to claim 1, wherein phytoplankton is allowed to grow such that:
the aquatic environment has a first Secchi disk visibility of between 60 cm to 30 cm during the first predetermined period;
the aquatic environment has a second Secchi disk visibility of between 40 cm to 20 cm during the second predetermined period; and
the aquatic environment has a third Secchi disk visibility of between 70 cm to about 60 cm during the third predetermined period.

11. The method according to claim 1, further comprising supplying at least one additional feed for the at least one farmed organism to grow, the additional feed being supplied in a ratio of 1:A:B in the first, second and third predetermined periods respectively, wherein A is between 3 to 15 and/or B is between 0 to 30.

12. The method according to claim 11, wherein A is between 5 to 10 and/or B is between 15 to 20.

13. The method according to claim 1, further comprising supplying at least one mineral and/or vitamin, wherein the at least one mineral and/or vitamin is in a bioavailable form suitable for allowing the at least one farmed organism, the phytoplankton and/or the bacteria to grow.

14. The method of claim 13, wherein the at least one mineral and/or vitamin is supplied in a gradually increasing amount suitable for allowing the at least one farmed organism, the phytoplankton and/or the bacteria to grow.

15. The method of claim 13, wherein at least one mineral is supplied in an amount suitable for maintaining the pH of the aquatic environment between 7.5 to 8.5.

16. The method according to claim 1, wherein the phytoplankton allowed to grow comprises at least one green algae and/or at least one diatom species.

17. The method according to claim 1, wherein at least one of the supplied bacteria and/or the bacteria allowed to grow comprises at least one species of bacteria that is probiotic with respect to the at least one farmed organism.

18. The method according to claim 1, wherein at least one of the supplied bacteria and/or the bacteria allowed to grow is capable of maintaining the concentration of ammonia and/or nitrites and/or nitrates in the aquatic environment at a level that is not toxic to the at least one farmed organism.

19. The method according to claim 1, wherein the bacteria allowed to grow comprises at least one species of nitrifying bacteria.

20. The method according to claim 1, wherein at least one of the supplied bacteria and/or the bacteria allowed to grow comprises at least one species of denitrifying bacteria.

21. The method according to claim 1, wherein at least one of the supplied bacteria and/or the bacteria allowed to grow comprises at least one species of aerobic and/or facultative anaerobic bacteria.

22. The method according to claim 1, wherein the at least one phytoplankton nutrient supplied comprises calcium, magnesium, potassium and sodium in forms and quantities suitable to grow phytoplankton that is not toxic or pathogenic to the at least one farmed organism.

23. The method according to claim 1, wherein the at least one phytoplankton nutrient is supplied in an amount suitable for maintaining an N:P ratio in the aquatic environment between 16 to 20.

24. The method according to claim 1, wherein the at least one bacteria nutrient is supplied in an amount suitable for maintaining a C:N ratio in the aquatic environment suitable to grow bacteria that is not toxic to the at least one farmed organism.

25. The method according to claim 1, wherein the at least one bacteria nutrient is supplied in an amount suitable for maintaining a C:N ratio in the aquatic environment suitable to grow bacteria that is capable of maintaining the concentration of ammonia and/or nitrites and/or nitrates in the aquatic environment at a level that is not toxic to the at least one farmed organism.

26. The method according to claim 24, wherein the C:N ratio is between 6 to 10.

27. The method according to claim 24, wherein the at least one bacteria nutrient supplied comprises at least one carbon source.

28. The method according to claim 1, wherein the at least one bacteria nutrient is supplied in an amount suitable for maintaining an Oxidation Reduction Potential (ORP) in the aquatic environment of between +100 mV to +350 mV.

29. The method according to claim 1, wherein the at least one bacteria nutrient supplied comprises micronutrients in forms and quantities suitable to grow bacteria that is not toxic or pathogenic to the at least one farmed organism.

30. The method according to claim 1, wherein the bacteria nutrient supplied comprises micronutrients in forms and quantities suitable to grow bacteria that is capable of maintaining the concentration of ammonia and/or nitrites and/or nitrates in the aquatic environment at a level that is not toxic to the at least one farmed organism.

31. The method according to claim 1, wherein the aquatic environment comprises a water phase and a soil phase in a pond, and a layer of organic matter and/or a cavity in fluid communication with the water phase.

32. The method according to claim 1, wherein in the third predetermined period, the at least one farmed organism, phytoplankton and bacteria present in the aquatic environment are substantially chemoautotrophic and heterotrophic.

33. The method according to claim 1, wherein the method does not comprise discharging water from the aquatic environment during at least one of the first, second and/or third predetermined periods.

34. The method according to claim 1, wherein the method does not comprise discharging water from the aquatic environment during any of the first, second and/or third predetermined periods.

35. The method according to claim 1, wherein the at least one farmed organism is not phytoplankton or bacteria.

36. The method according to claim 1, wherein the at least one farmed organism is selected from the group consisting of: fish, crustaceans, mollusks, seaweeds and/or invertebrates.

37. The method according to claim 1, wherein the at least one farmed organism is selected from the group consisting of: Tilapias, Catfishes, Milkfishes, Groupers, Barramundi, Carps, Snakeheads, Catlas, Sturgeons, Eels, Mullets, Rohus, Seabasses, Seabreams, Rabbit fishes, Shrimps, Prawns, Crabs, Lobsters, Crayfishes, Oysters, Clams, Mussels, Scallops, Carpet shells, Abalones, Sea cucumbers, and/or Sea urchins.

38. The method according to claim 1, wherein the at least one farmed organism is fish and/or shrimp.

39. The method according to claim 1, further comprising determining a desired production cycle length for the at least one farmed organism, and wherein:
- the first predetermined period is from 30% to 50% of the desired production cycle length and begins with stocking of the aquatic environment;
- the second predetermined period is from 30% to 50% of the desired length of production cycle length, begins with the end of the first predetermined period and ends with the start of the third predetermined period; and
- the third predetermined period is from 0% to 40% of the desired production cycle length, begins with the end of the second predetermined period and ends with the harvesting of the at least one farmed organism.

40. The method according to claim 1, wherein:
- the first predetermined period is from 30% to 40% of the desired production cycle length and begins with stocking of the aquatic environment;
- the second predetermined period is from 30% to 40% of the desired length of production cycle length, begins with the end of the first predetermined period and ends with the start of the third predetermined period; and
- the third predetermined period is from 30% to 40% of the desired production cycle length, begins with the end of the second predetermined period and ends with the harvesting of the at least one farmed organism.

41. The method according to claim 1, wherein the at least one farmed organism comprises shrimp, the first predetermined period is between 35 to 40 days, the second predetermined period is between 35 to 40 days and the third predetermined period in the desired production cycle is at least for 5 days and ends with the harvest of the at least one farmed organism.

42. The method according to claim 1, wherein the at least one farmed organism comprises shrimp, and the method further comprises stocking at least 200 shrimp per square meter of the aquatic environment at the start of the first predetermined period.

43. The method according to claim 1, wherein the at least one farmed organism comprises shrimp, and the method further comprises stocking at least 300 shrimp per square meter of the aquatic environment at the start of the first predetermined period.

44. The method according to claim 11, wherein allowing the farmed organisms to grow increases the mass of the farmed organisms by at least 0.7 times the mass of the at least one additional feed supplied from the start of the first predetermined period to the end of the third predetermined period.

* * * * *